United States Patent
Hornsperger et al.

(10) Patent No.: US 9,980,929 B2
(45) Date of Patent: May 29, 2018

(54) TRIFLUOROMETHYLPROPANAMIDE DERIVATIVES

(71) Applicant: Hoffmann-La Roche Inc., Little Falls, NJ (US)

(72) Inventors: Benoit Hornsperger, Altkirch (FR); Roberto Iacone, Basel (CH); Bernd Kuhn, Reinach BL (CH); Hans P. Maerki, Basel (CH); Peter Mohr, Basel (CH); Michael Reutlinger, Freiburg (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/683,341

(22) Filed: Aug. 22, 2017

(65) Prior Publication Data
US 2017/0348257 A1    Dec. 7, 2017

Related U.S. Application Data

(63) Continuation of application No. PCT/EP2016/053618, filed on Feb. 22, 2016.

(30) Foreign Application Priority Data

Feb. 25, 2015   (EP) .................... 15156501

(51) Int. Cl.
| C07D 213/06 | (2006.01) |
| C07D 241/12 | (2006.01) |
| A61K 31/165 | (2006.01) |
| A61K 31/4402 | (2006.01) |
| A61K 31/4406 | (2006.01) |
| A61K 31/4965 | (2006.01) |
| C07C 237/22 | (2006.01) |

(52) U.S. Cl.
CPC ........ *A61K 31/165* (2013.01); *A61K 31/4402* (2013.01); *A61K 31/4406* (2013.01); *A61K 31/4965* (2013.01); *C07C 237/22* (2013.01); *C07D 213/06* (2013.01); *C07D 241/12* (2013.01); *C07B 2200/07* (2013.01)

(58) Field of Classification Search
CPC ........................... C07D 213/06; C07D 241/12
See application file for complete search history.

(56) References Cited

FOREIGN PATENT DOCUMENTS

| WO | 00/61542 A1 | 10/2000 |
| WO | 2014/086805 A1 | 6/2014 |

*Primary Examiner* — Brian E McDowell
(74) *Attorney, Agent, or Firm* — Brian L. Buckwalter

(57) ABSTRACT

The invention provides novel compounds having the general formula (I)

wherein $R^1$, $R^2$, $R^3$, $R^4$, $R^5$, $R^6$ and $R^7$ are as described herein, compositions including the compounds and methods of using the compounds.

26 Claims, No Drawings

TRIFLUOROMETHYLPROPANAMIDE DERIVATIVES

CROSS REFERENCE TO RELATED APPLICATIONS

This application is a continuation of International Application No. PCT/EP2016/053618 having an international filing date of Feb. 22, 2016 and which claims benefit under 35 U.S.C. § 119 to European Patent Application No. 15156501.7 filed Feb. 25, 2015. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Inhibition of the serine protease HtrA1, which belongs to an evolutionarily conserved family of HtrA proteins, has the potential to protect and treat tissue damage caused by the degeneration of retinal or photoreceptor cells in the human eye. The pathophysiological relevance of HtrA1 in the progression of the age-related macular degeneration has been firmly established by human genetic studies where a SNP in the HtrA1 promoter region results in increased HtrA1 transcript and protein levels. Age-related macular degeneration is the leading cause of severe irreversible central vision loss and blindness in individuals over 65 years of age in developed countries. There are two forms of AMD: dry AMD and wet AMD. Wet AMD (also known as exudative AMD), is associated with pathologic posterior choroidal neovascularization subsequent to the disruption of the delimiting Bruch's membrane. Tissue edema due to the leakage from the abnormal blood vessels damages the macula and impairs vision, eventually leading to blindness. In dry AMD, drusen have been reported in the macula of the eye, the cells in the macula die for the progressive accumulation of the drusen, resulting in progressive vision loss. Dry AMD is clinically described to occur in three stages: 1) early, 2) intermediate, and 3) advanced dry AMD. Dry AMD can also progress into wet AMD during any stage of the disease. Treatment strategies for wet AMD exists and the current standard of care is Lucentis (Genentech/Roche) and Eylea (Regeneron), an anti-VEGF antibody and an anti-VEGF trap injected intravitreally respectively. There are no current treatments for preventing loss of vision for the dry form and for preventing progression of dry AMD to local atrophy of the retinal tissue. As discussed above, HtrA1 risk alleles have been associated, with high statistical significance, with the AMD onsets and the protein has been reported to be present in drusen. These studies and further evidences provide relevance that HtrA1 is a fundamental factor involved in the pathophysiology and progression in AMD. This concept is further confirmed in different AMD disease models, where increased HtrA1 protein levels in the retina tissue have been shown to be responsible for the degradation of extracellular matrix (ECM) proteins like fibronectin, fibulins and aggrecan. The physiological balance between production and disintegration of the ECM components allows for both creation and maintenance of proper retina tissue architecture. Such balance has been reported to be lost in the progression of the age-related macular degeneration. In particular, the fibulins (mainly-3, -5, -6) have been reported to be important components of the Bruch's membrane in maintaining the integrity of elastic lamina and organization of the retina tissue overall. Several variants in fibulin 5 and fibulin 3 were reported to be associated with AMD. Missense mutations of the fibulin 5 gene have been associated with reduced secretion of fibulin 5. Different studies have reported that Htra1 protease activity is directed to the cleavage of the fibulins as substrates. A direct inhibition of HtrA1 protease activity is expected to provide a protection reducing degradation of extracellular matrix proteins, in particular fibulins and fibrionectin, therefore preserving the retina tissue structure. The relevance of HtrA1's role in maintenance of the physiological homeostasis of the ECM components is firmly provided by the identification of human loss-of-function mutations causing familial ischemic cerebral small-vessel disease. The molecular mechanism underlies in the deficient TGFbeta inhibition by HtrA1 resulting in increased signaling levels, which in conjunction with deficient HtrA1-mediated degradation of various extracellular matrix components determine thickening of the intima responsible for the ischemic small-vessels. Given its fundamental role in regulating intracellular signaling pathways (e.g. TGFbeta) and the regulation of ECM proteins turnover, HtrA1 has been involved in several pathologies, as ocular diseases, rheumatoid arthritis, osteoarthritis, Alzheimer's disease, and some types of cancer.

BRIEF SUMMARY OF THE INVENTION

The present invention provides novel compounds of formula (I)

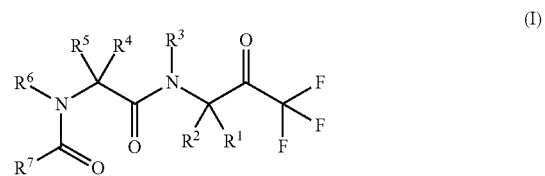

wherein
$R^1$ is alkyl, haloalkyl or cycloalkyl;
$R^2$ is H, alkyl, haloalkyl or cycloalkyl;
$R^3$ is H, alkyl or cycloalkyl;
$R^4$ is optionally substituted aryl, optionally substituted arylalkyl, optionally substituted heteroaryl or optionally substituted heteroarylalkyl, wherein each moiety is optionally substituted by one to three substituents independently selected from halogen, alkyl, haloalkyl, cycloalkyl, cyano, hydroxy, alkoxy or haloalkoxy;
$R^5$ is H, alkyl, haloalkyl or cycloalkyl;
$R^6$ is H, alkyl or cycloalkyl;
$R^7$ is optionally substituted adamantanylalkyl, optionally substituted cycloalkyl, optionally substituted cycloalkylalkyl, optionally substituted dicycloalkylalkyl, optionally substituted heterocycloalkylarylalkyl, optionally substituted aryloxycycloalkylalkyl, optionally substituted aryl, optionally substituted arylalkyl, optionally substituted arylalkenyl, optionally substituted diarylalkyl, optionally substituted aryloxyalkyl, optionally substituted diaryloxyalkyl, optionally substituted arylaryloxyalkyl, optionally substituted heteroaryl, optionally substituted heteroarylalkyl, optionally substituted heteroarylalkenyl, optionally substituted arylheteroarylalkyl or optionally substituted aryloxyheteroarylalkyl, wherein the optional substituents are one to three groups independently selected from halogen, alkyl, haloalkyl, cycloalkyl, cyano, hydroxy, alkoxy, haloalkoxy or phenyl;

or pharmaceutically acceptable salts.

In another embodiment, the present inventions provide for pharmaceutical compositions comprising compounds of Formula I.

DETAILED DESCRIPTION OF THE INVENTION

The present invention relates to organic compounds useful for therapy or prophylaxis in a mammal, and in particular to serine protease HtrA1 inhibitors for the treatment or prophylaxis of HtrA1-mediated ocular diseases, such as wet or dry age-related macular degeneration, geographic atrophy, diabetic retinopathy, retinopathy of prematurity and polypoidal choroidal vasculopathy.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of HtrA1, particularly in the treatment or prophylaxis of wet or dry age-related macular degeneration, geographic atrophy, diabetic retinopathy, retinopathy of prematurity and polypoidal choroidal vasculopathy.

The term "adamantanylalkyl" denotes an alkyl group wherein one of the hydrogen atoms of the alkyl group has been replaced by an adamantanyl. Particular adamantanylalkyl group is adamantanylmethyl.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular example is methoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, tert-butyl and pentyl. Particular alkyl group is isopropyl.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "arylalkenyl" denotes an alkenyl group wherein one of the hydrogen atoms of the alkyl group has been replaced by an aryl group. Particular arylalkenyl group is phenylalkenyl. Particular example of arylalkenyl is phenylethylenyl.

The term "arylalkyl" denotes an alkyl group wherein one of the hydrogen atoms of the alkyl group has been replaced by an aryl group. Particular arylalkyl group is phenylalkyl. Particular examples of arylalkyl are phenylmethyl and phenylethyl.

The term "arylaryloxyalkyl" denotes an alkyl group wherein one of the hydrogen atoms of the alkyl group has been replaced by an aryl group and another one of the hydrogen atoms of the alkyl group has been replaced by an aryloxy group. Particular arylaryloxyalkyl group is phenylphenoxyalkyl. Particular examples of arylaryloxyalkyl are phenylphenoxymethyl and phenylphenoxyethyl.

The term "aryloxycycloalkylalkyl" denotes an alkyl group wherein one of the hydrogen atoms of the alkyl group has been replaced by an aryloxy group and another one of the hydrogen atoms of the alkyl group has been replaced by a cycloalkyl group. Particular aryloxycycloalkylalkyl is phenoxycycloalkylalkyl, more particularly phenoxyhexanylalkyl.

The term "arylheteroarylalkyl" denotes an alkyl group wherein one of the hydrogen atoms of the alkyl group has been replaced by an aryl group and another one of the hydrogen atoms of the alkyl group has been replaced by a heteroaryl group.

The term "aryloxy" denotes a group of the formula —O—R', wherein R' is an aryl group. Particular examples of aryloxy group are groups wherein R' is phenyl.

The term "aryloxyalkyl" denotes an alkyl group wherein one of the hydrogen atoms of the alkyl group has been replaced by an aryloxy group. Particular example of aryloxyalkyl is phenoxyalkyl. Further particular example is phenoxymethyl.

The term "aryloxyheteroarylalkyl" denotes an alkyl group wherein one of the hydrogen atoms of the alkyl group has been replaced by an aryloxy group and another one of the hydrogen atoms of the alkyl group has been replaced by a heteroaryl group.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cyano" denotes a —C≡N group.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclohexyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Further particular examples cycloalkylalkyl is cyclohexylethyl.

The term "diarylalkyl" denotes an alkyl group wherein two of the hydrogen atoms of the alkyl group have been replaced by two independently selected aryl groups. Particular diarylalkyl group is diphenyl alkyl. Examples of diarylalkyl are diphenylmethyl and diphenylethyl. Particular example of diarylalkyl is phenyl ethyl. Further particular examples are 1,2-diphenylethyl and 2,2-diphenylethyl.

The term "diaryloxyalkyl" denotes an alkyl group wherein two of the hydrogen atoms of the alkyl group have been replaced by two independently selected aryloxy groups. Particular diaryloxyalkyl group is diphenoxyalkyl. Particular example of diaryloxyethyl is 1,2-diphenoxyethyl.

The term "dicycloalkylalkyl" denotes an alkyl group wherein two of the hydrogen atoms of the alkyl group have been replaced by two independently selected cycloalkyl groups.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups is trifluoromethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halogen" and "halo" are used interchangeably herein and denote fluoro, chloro, bromo or iodo. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl. Particular heteroaryl groups are pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, isoxazolyl, isothiazolyl, benzofuranyl and benzothiophenyl. More particular heteroaryl groups are imidazolyl, oxazolyl, thiazolyl, oxadiazolyl, thiadiazolyl, tetrazolyl, pyridinyl, pyrazinyl, pyrazolyl, pyridazinyl, pyrimidinyl, isoxazolyl, isothiazolyl, benzofuranyl and benzothiophenyl. Furthermore particular heteroaryl groups include are pyridinyl, benzofuranyl and benzothiophenyl. In the case of substituent $R^7$, particular heteroarylalkyl groups are benzofuranyl and benzothiophenyl.

The term "heteroarylalkyl" denotes an alkyl group wherein one of the hydrogen atoms of the alkyl group has been replaced by a heteroaryl group. In the case of substituent $R^4$, particular heteroarylalkyl group is pyridinylalkyl.

The term "heteroarylalkenyl" denotes an alkenyl group wherein one of the hydrogen atoms of the alkyl group has been replaced by a heteroaryl group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl.

The term "heterocycloalkylarylalkyl" denotes an alkyl group wherein one of the hydrogen atoms of the alkyl group has been replaced by a heterocycloalkyl group and another one of the hydrogen atoms of the alkyl group has been replaced by an aryl group. In the case of substituent $R^7$, particular heterocycloalkylarylalkyl group is an alkyl group wherein the heterocycloalkyl group is 1,1-dioxo-1,4-thiazinanyl and the aryl group is phenyl.

The term "phenoxy" denotes a group of the formula —O—R', wherein R' is a phenyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

"Optional" or "optionally" means that the subsequently described event or circumstance may but need not occur, and that the description includes instances where the event or circumstance occurs and instances in which it does not.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

$R^1$ is alkyl, haloalkyl or cycloalkyl;
$R^2$ is H, alkyl, haloalkyl or cycloalkyl;
$R^3$ is H, alkyl or cycloalkyl;
$R^4$ is substituted aryl, substituted arylalkyl, substituted heteroaryl or substituted heteroarylalkyl, wherein substituted aryl, substituted arylalkyl, substituted heteroaryl and substituted heteroarylalkyl are substituted by one to three substituents independently selected from H, halogen, alkyl, haloalkyl, cycloalkyl, cyano, hydroxy, alkoxy and haloalkoxy;
$R^5$ is H, alkyl, haloalkyl or cycloalkyl;
$R^6$ is H, alkyl or cycloalkyl;
$R^7$ is substituted adamantanylalkyl, substituted cycloalkyl, substituted cycloalkylalkyl, substituted dicycloalkylalkyl, substituted aryl, substituted arylalkyl, substituted arylalkenyl, substituted diarylalkyl, substituted aryloxyalkyl, substituted diaryloxyalkyl, substituted arylaryloxyalkyl, substituted heteroaryl, substituted heteroarylalkyl, substituted heteroarylalkenyl, substituted arylheteroarylalkyl or substituted aryloxyheteroarylalkyl, wherein substituted adamantanylalkyl, substituted cycloalkyl, substituted cycloalkylalkyl, substituted dicycloalkylalkyl, substituted aryl, substituted arylalkyl, substituted arylalkenyl, substituted diarylalkyl, substituted aryloxyalkyl, substituted diaryloxyalkyl, substituted arylaryloxyalkyl, substituted heteroaryl, substituted heteroarylalkyl, substituted heteroarylalkenyl, substituted arylheteroarylalkyl and substituted aryloxyheteroarylalkyl are substituted by one to three substituents independently selected from H, halogen, alkyl, haloalkyl, cycloalkyl, cyano, hydroxy, alkoxy, haloalkoxy and phenyl;
or pharmaceutically acceptable salts.

Another embodiment of the present invention are compounds according to formula (I) as described herein, wherein $R^1$ is alkyl.

Also an embodiment of the present invention are compounds according to formula (I) as described herein, wherein $R^2$ is H.

A particular embodiment of the present invention are compounds according to formula (I) as described herein, wherein $R^3$ is H and alkyl.

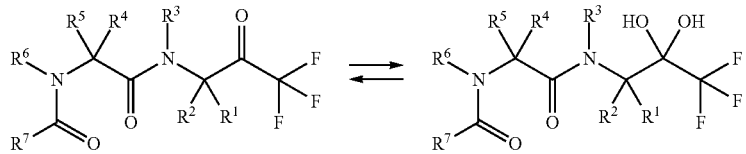

Depending on the individual compound and the conditions it has been exposed, the $CF_3$-ketone moieties in compounds I exist in part, mainly or totally in form of its hydrate. Thus, any description of a $CF_3$-ketone moiety always describes both ketone and hydrate form.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein In a further particular embodiment of the present invention are compounds according to formula (I) as described herein, wherein $R^3$ is H.

A more particular embodiment of the present invention are compounds according to formula (I) as described herein, wherein $R^4$ is substituted phenyl, substituted phenylalkyl or substituted pyridinylalkyl, wherein substituted phenyl, substituted phenylalkyl and substituted pyridinylalkyl are substituted by one to three substituents independently selected from H, alkoxy or halogen.

A further more particular embodiment of the present invention are compounds according to formula (I) as described herein, wherein $R^4$ is phenylalkyl, phenyl, phenyl substituted by one alkoxy or phenylalkyl substituted by one halogen.

A further more particular embodiment of the present invention are compounds according to formula (I) as described herein, wherein $R^4$ is phenylmethyl, phenyl, methoxyphenyl or chlorophenylmethyl.

The present invention also relates to compounds according to formula (I) as described herein, wherein $R^5$ is H.

A particular embodiment of the present invention are compounds according to formula (I) as described herein, wherein $R^6$ is H.

Another embodiment of the present invention are compounds according to formula (I) as described herein, wherein $R^7$ is substituted cycloalkylalkyl, substituted phenylalkyl, substituted phenylalkenyl, substituted diphenylalkyl, substituted phenoxyalkyl, substituted phenylphenoxyalkyl, substituted benzofuranyl or substituted benzothiophenyl, wherein substituted cycloalkylalkyl, substituted phenylalkyl, substituted phenylalkenyl, substituted diphenylalkyl, substituted phenoxyalkyl, substituted phenylphenoxyalkyl, substituted benzofuranyl and substituted benzothiophenyl are substituted by one to three substituents independently selected from H, halogen, alkoxy and phenyl.

Also an embodiment of the present invention are compounds according to formula (I) as described herein, wherein $R^7$ is substituted phenylalkenyl, substituted diphenylalkyl, substituted phenoxyalkyl or substituted phenylphenoxyalkyl, wherein substituted phenylalkenyl, substituted diphenylalkyl, substituted phenoxyalkyl and substituted phenylphenoxyalkyl are substituted by one to three substituents independently selected from H and halogen.

Also an embodiment of the present invention are compounds according to formula (I) as described herein, wherein $R^7$ is 2-chlorophenyl-2-phenylmethyl, dichlorophenoxymethyl, dichlorophenylethylenyl or 2-dichlorophenoxy-2-phenylmethyl.

Another embodiment of the present invention are compounds according to formula (I) as described herein, wherein the compound is of formula (Ia).

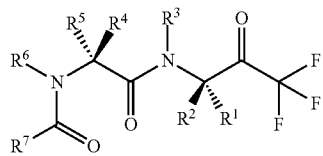

(Ia)

Another embodiment of the present invention are compounds according to formula (I) as described herein, wherein
$R^1$ is alkyl;
$R^2$, $R^3$, $R^5$ and $R^6$ are H;
$R^4$ is phenylalkyl, phenyl, phenyl substituted by one alkoxy or phenylalkyl substituted by one halogen;
$R^7$ is substituted phenylalkenyl, substituted diphenylalkyl, substituted phenoxyalkyl or substituted phenylphenoxyalkyl, wherein substituted phenylalkenyl, substituted diphenyl alkyl, substituted phenoxyalkyl and substituted phenylphenoxyalkyl are substituted by one to three substituents independently selected from H and halogen;
or pharmaceutically acceptable salts Particular examples of compounds of formula (I) as described herein are selected from
(2S)-2-[3,4-Dichlorophenyl)propanoylamino]-3-phenyl-N-[(3S)-1,1,1-trifluoro-4-methyl-2-oxopentan-3-yl]propanamide;
(2S)-2-[[2-(3-Chlorophenoxy)acetyl]amino]-3-phenyl-N-[(3S)-1,1,1-trifluoro-4-methyl-2-oxopentan-3-yl]propanamide;
(2S)-2-[[2-(3,4-Dichlorophenoxy)acetyl]amino]-3-phenyl-N-[(3S)-1,1,1-trifluoro-4-methyl-2-oxopentan-3-yl]propanamide;
(2S)-2-[[(3R/S)-(3-Chlorophenyl)-3-phenylpropanoyl]amino]-3-phenyl-N-[(3S)-1,1,1-trifluoro-4-methyl-2-oxopentan-3-yl]propanamide;
(2S)-2-(3,3-Diphenylpropanoylamino)-3-phenyl-N-[(3S)-1,1,1-trifluoro-4-methyl-2-oxopentan-3-yl]propanamide;
(2S)-2-[[(3R/S)-(4-Chlorophenyl)-3-(4-methoxyphenoxy)propanoyl]amino]-3-phenyl-N-[(3S)-1,1,1-trifluoro-4-methyl-2-oxopentan-3-yl]propanamide;
(2S)-3-(4-Chlorophenyl)-2-[[(3R/S)-(4-chlorophenyl)-3-(4-methoxyphenoxy)propanoyl]amino]-N-[(3S)-1,1,1-trifluoro-4-methyl-2-oxopentan-3-yl]propanamide;
(2S)-2-[[(E)-3-(4-Chlorophenyl)prop-2-enoyl]amino]-3-phenyl-N-[(3S)-1,1,1-trifluoro-4-methyl-2-oxopentan-3-yl]propanamide;
(2S)-3-(4-Chlorophenyl)-2-[[(3R/S)-(4-chlorophenyl)-3-(4-methoxyphenyl)propanoyl]amino]-N-[(3S)-1,1,1-trifluoro-4-methyl-2-oxopentan-3-yl]propanamide;
(2S)-3-(4-Chlorophenyl)-2-[[(3R/S)-(4-chlorophenyl)-3-phenylpropanoyl]amino]-N-[(3S)-1,1,1-trifluoro-4-methyl-2-oxopentan-3-yl]propanamide;
(2S)-3-(4-Chlorophenyl)-2-[[(3R/S)-(3-chlorophenyl)-3-(4-methoxyphenoxy)propanoyl]amino]-N-[(3S)-1,1,1-trifluoro-4-methyl-2-oxopentan-3-yl]propanamide;
(2S)-3-(4-Chlorophenyl)-2-[[(3R/S)-(3,4-dichlorophenyl)-3-(4-methoxyphenyl)propanoyl]amino]-N-[(3S)-1,1,1-trifluoro-4-methyl-2-oxopentan-3-yl]propanamide;
(2S)-2-[[(3R/S)-(4-Chlorophenyl)-3-(4-methoxyphenyl)propanoyl]amino]-3-pyridin-2-yl-N-[(3S)-1,1,1-trifluoro-4-methyl-2-oxopentan-3-yl]propanamide;
(2S)-3-(4-Chlorophenyl)-2-[[(E)-3-(3,4-dichlorophenyl)prop-2-enoyl]amino]-N-[(3S)-1,1,1-trifluoro-4-methyl-2-oxopentan-3-yl]propanamide;
(2S)-3-(3-Chlorophenyl)-2-[3-(3,4-dichlorophenyl)propanoylamino]-N-[(3S)-1,1,1-trifluoro-4-methyl-2-oxopentan-3-yl]propanamide;
(2S)-3-(3-Chlorophenyl)-2-[[(3R/S)-(3,4-dichlorophenyl)-3-(4-methoxyphenyl)propanoyl]amino]-N-[(3S)-1,1,1-trifluoro-4-methyl-2-oxopentan-3-yl]propanamide;
(2S)-3-(3-Chlorophenyl)-2-[[(3R/S)-(4-chlorophenyl)-3-(4-methoxyphenyl)propanoyl]amino]-N-[(3S)-1,1,1-trifluoro-4-methyl-2-oxopentan-3-yl]propanamide;
(2S)-3-(3-Chlorophenyl)-2-[[(3R/S)-(4-chlorophenyl)-3-(4-methoxyphenoxy)propanoyl]amino]-N-[(3S)-1,1,1-trifluoro-4-methyl-2-oxopentan-3-yl]propanamide;
(2S)-3-(3-Chlorophenyl)-2-[[(E)-3-(3,4-dichlorophenyl)prop-2-enoyl]amino]-N-[(3S)-1,1,1-trifluoro-4-methyl-2-oxopentan-3-yl]propanamide;
(2S)-3-(3-Chlorophenyl)-2-[3-(3,5-dichlorophenyl)propanoylamino]-N-[(3S)-1,1,1-trifluoro-4-methyl-2-oxopentan-3-yl]propanamide;
(2S)-3-(4-Chlorophenyl)-2-[[2-(3,5-dichlorophenoxy)acetyl]amino]-N-[(3S)-1,1,1-trifluoro-4-methyl-2-oxopentan-3-yl]propanamide;
(2S)-3-(4-Chlorophenyl)-2-[[(E)-3-(3,5-dichlorophenyl)prop-2-enoyl]amino]-N-[(3S)-1,1,1-trifluoro-4-methyl-2-oxopentan-3-yl]propanamide;
3-(3,4-Dichlorophenyl)-N-[(1S and 1R)-2-oxo-1-phenyl-2-[[(3S)-1,1,1-trifluoro-4-methyl-2-oxopentan-3-yl]amino]ethyl]propanamide;

(3R/S)-(3-Chlorophenyl)-N-[(1S and 1R)-2-oxo-1-phenyl-2-[[(3S)-1,1,1-trifluoro-4-methyl-2-oxopentan-3-yl]amino]ethyl]-3-phenylpropanamide;

(2S)-2-[[2-(3-Chlorophenoxy)acetyl]-methyl amino]-3-phenyl-N-[(3S)-1,1,1-trifluoro-4-methyl-2-oxopentan-3-yl]propanamide;

(2S)-2-[[(3R/S)-(3-Chlorophenyl)-3-phenylpropanoyl]-methylamino]-3-phenyl-N-[(3S)-1,1,1-trifluoro-4-methyl-2-oxopentan-3-yl]propanamide;

5-Chloro-N-[(2S)-3-(3-chlorophenyl)-1-oxo-1-[[(3S)-1,1,1-trifluoro-4-methyl-2-oxopentan-3-yl]amino]propan-2-yl]-1-benzothiophene-3-carboxamide;

(E)-3-(3,4-Dichlorophenyl)-N-[(1S and 1R)-2-oxo-1-phenyl-2-[[(3S)-1,1,1-trifluoro-4-methyl-2-oxopentan-3-yl]amino]ethyl]prop-2-enamide;

(2S and 2R)-2-[[2-(3,5-Dichlorophenoxy)acetyl]amino]-2-phenyl-N-[(3S)-1,1,1-trifluoro-4-methyl-2-oxopentan-3-yl]acetamide;

N-[(1S and 1R)-1-(4-Chlorophenyl)-2-oxo-2-[[(3S)-1,1,1-trifluoro-4-methyl-2-oxopentan-3-yl]amino]ethyl]-3-(3,4-dichlorophenyl)propanamide;

(3R/S)-(3-Chlorophenyl)-N-[(1 S and 1R)-1-(4-chlorophenyl)-2-oxo-2-[[(3S)-1,1,1-trifluoro-4-methyl-2-oxopentan-3-yl]amino]ethyl]-3-phenylpropanamide;

(2S)-3-(3-Chlorophenyl)-2-[[(3R/S)-(3,4-dichlorophenyl)-3-(4-methoxyphenoxy)propanoyl]amino]-N-[(3S)-1,1,1-trifluoro-4-methyl-2-oxopentan-3-yl]propanamide;

(E)-N-[(1S and 1R)-1-(4-Chlorophenyl)-2-oxo-2-[[(3S)-1,1,1-trifluoro-4-methyl-2-oxopentan-3-yl]amino]ethyl]-3-(3,4-dichlorophenyl)prop-2-enamide;

3-(4-Chlorophenyl)-N-[(2S)-3-(3-chlorophenyl)-1-oxo-1-[[(3S)-1,1,1-trifluoro-4-methyl-2-oxopentan-3-yl]amino]propan-2-yl]-(2R/S)-(4-methoxyphenyl)propanamide;

(2S and 2R)-2-(4-Chlorophenyl)-2-[[2-(3,5-dichlorophenoxy)acetyl]amino]-N-[(3S)-1,1,1-trifluoro-4-methyl-2-oxopentan-3-yl]acetamide;

(2S and 2R)-2-[[(2R/S)-(3,5-Dichlorophenoxy)-2-phenyl acetyl]amino]-2-phenyl-N-[(3S)-1,1,1-trifluoro-4-methyl-2-oxopentan-3-yl]acetamide;

6-Chloro-N-[(1S and 1R)-2-oxo-1-phenyl-2-[[(3S)-1,1,1-trifluoro-4-methyl-2-oxopentan-3-yl]amino]ethyl]-3-phenyl-1-benzofuran-2-carboxamide;

7-Bromo-5-chloro-N-[(1S and 1R)-2-oxo-1-phenyl-2-[[(3S)-1,1,1-trifluoro-4-methyl-2-oxopentan-3-yl]amino]ethyl]-1-benzofuran-2-carboxamide;

3-Cyclohexyl-N-[(1S and 1R)2-oxo-1-phenyl-2-[[(3S)-1,1,1-trifluoro-4-methyl-2-oxopentan-3-yl]amino]ethyl]propanamide;

5,7-Dichloro-N-[(1S and 1R)-2-oxo-1-phenyl-2-[[(3S)-1,1,1-trifluoro-4-methyl-2-oxopentan-3-yl]amino]ethyl]-3-phenyl-1-benzofuran-2-carboxamide;

(2S and 2R)-2-[[2-(2-Adamantyl)acetyl]amino]-2-phenyl-N-[(3S)-1,1,1-trifluoro-4-methyl-2-oxopentan-3-yl]acetamide;

(2S,3S)-2-[3-(3,4-Dichlorophenyl)propanoylamino]-3-phenyl-N-[(3S)-1,1,1-trifluoro-4-methyl-2-oxopentan-3-yl]butanamide;

(2S,3S)-2-[[(3R/S)-(3-Chlorophenyl)-3-phenylpropanoyl]amino]-3-phenyl-N-[(3S)-1,1,1-trifluoro-4-methyl-2-oxopentan-3-yl]butanamide;

(2S)-2-[3-(3,4-Dichlorophenyl)propanoylamino]-4-phenyl-N-[(3S)-1,1,1-trifluoro-4-methyl-2-oxopentan-3-yl]butanamide;

(2S)-2-[[(3R/S)-(3-Chlorophenyl)-3-phenylpropanoyl]amino]-4-phenyl-N-[(3S)-1,1,1-trifluoro-4-methyl-2-oxopentan-3-yl]butanamide;

3-(3,4-Dichlorophenyl)-N-[(1S or 1R)-1-(3-methoxyphenyl)-2-oxo-2-[[(3S)-1,1,1-trifluoro-4-methyl-2-oxopentan-3-yl]amino]ethyl]propanamide;

3-(3,4-Dichlorophenyl)-N-[(1R or 1S)-1-(3-methoxyphenyl)-2-oxo-2-[[(3S)-1,1,1-trifluoro-4-methyl-2-oxopentan-3-yl]amino]ethyl]propanamide;

(2S or 2R)-2-[[2-(3,5-Dichlorophenoxy)acetyl]amino]-2-(3-methoxyphenyl)-N-[(3S)-1,1,1-trifluoro-4-methyl-2-oxopentan-3-yl]acetamide;

(2R or 2 S)-2-[[2-(3,5-Dichlorophenoxy)acetyl]amino]-2-(3-methoxyphenyl)-N-[(3S)-1,1,1-trifluoro-4-methyl-2-oxopentan-3-yl]acetamide;

(E)-3-(3,4-Dichlorophenyl)-N-[(1S or 1R)-1-(3-methoxyphenyl)-2-oxo-2-[[(3S)-1,1,1-trifluoro-4-methyl-2-oxopentan-3-yl]amino]ethyl]prop-2-enamide;

(E)-3-(3,4-Dichlorophenyl)-N-[(1R or 1 S)-1-(3-methoxyphenyl)-2-oxo-2-[[(3S)-1,1,1-trifluoro-4-methyl-2-oxopentan-3-yl]amino]ethyl]prop-2-enamide;

(3R/S)-(3-Chlorophenyl)-N-[(1S or 1R)-1-(3-methoxyphenyl)-2-oxo-2-[[(3S)-1,1,1-trifluoro-4-methyl-2-oxopentan-3-yl]amino]ethyl]-3-phenylpropanamide;

(3R/S)-(3-Chlorophenyl)-N-[(1R or 1S)-1-(3-methoxyphenyl)-2-oxo-2-[[(3S)-1,1,1-trifluoro-4-methyl-2-oxopentan-3-yl]amino]ethyl]-3-phenylpropanamide;

and pharmaceutically acceptable salts thereof.

Also particular examples of compounds of formula (I) as described herein are selected from (2R)-2-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-phenylpropanamide;

(2R/S)-(3,4-Dichlorophenoxy)-3-(3,4-dichlorophenyl)-N-[(1S and 1R)-2-oxo-1-phenyl-2-[[(3S)-1,1,1-trifluoro-4-methyl-2-oxopentan-3-yl]amino]ethyl]propanamide;

(3R or 3S)-(4-Chlorophenyl)-2-(4-methoxyphenyl)-N-[(1S and 1R)-2-oxo-1-phenyl-2-[[(3S)-1,1,1-trifluoro-4-methyl-2-oxopentan-3-yl]amino]ethyl]propanamide;

(3S or 3R)-(4-Chlorophenyl)-2-(4-methoxyphenyl)-N-[(1 S and 1R)-2-oxo-1-phenyl-2-[[(3S)-1,1,1-trifluoro-4-methyl-2-oxopentan-3-yl]amino]ethyl]propanamide;

(3S or 3R)-(3,4-Dichlorophenyl)-3-(1,1-dioxo-1,4-thiazinan-4-yl)-N-[(1S and 1R)-2-oxo-1-phenyl-2-[[(3S)-1,1,1-trifluoro-4-methyl-2-oxopentan-3-yl]amino]ethyl]propanamide;

(3R or 3S)-(3,4-Dichlorophenyl)-3-(1,1-dioxo-1,4-thiazinan-4-yl)-N-[(1 S and 1R)-2-oxo-1-phenyl-2-[[(3S)-1,1,1-trifluoro-4-methyl-2-oxopentan-3-yl]amino]ethyl]propanamide;

(S)-2-(3-(3,5-Difluorophenyl)propanamido)-3-phenyl-N—((S)-1,1,1-trifluoro-4-methyl-2-oxopentan-3-yl)propanamide;

(R)-2-(3,5-Dichlorophenoxy)-N—((S)-1-oxo-3-phenyl-1-(((S)-1,1,1-trifluoro-4-methyl-2-oxopentan-3-yl)amino)propan-2-yl)-3-phenylpropanamide;

3-(3,5-Difluorophenyl)-N-[(1S and 1R)-2-oxo-1-phenyl-2-[[(3S)-1,1,1-trifluoro-4-methyl-2-oxopentan-3-yl]amino]ethyl]propanamide;

(R)-2-(3,5-Difluorophenoxy)-N-((1S and 1R)-2-oxo-1-phenyl-2-(((S)-1,1,1-trifluoro-4-methyl-2-oxopentan-3-yl)amino)ethyl)-3-phenylpropanamide;

(3R/S)-Cyclohexyl-2-(3,5-dichlorophenoxy)-N-[(1S and 1R)-2-oxo-1-phenyl-2-[[(3S)-1,1,1-trifluoro-4-methyl-2-oxopentan-3-yl]amino]ethyl]propanamide;

(2S and 2R)-2-[[2-(3,5-Difluorophenoxy)acetyl]amino]-2-phenyl-N-[(3S)-1,1,1-trifluoro-4-methyl-2-oxopentan-3-yl]acetamide;

(2S)-2-[[(2S/R)-3-Cyclohexyl-2-(3,5-dichlorophenoxy)propanoyl]amino]-3-phenyl-N-[(3S)-1,1,1-trifluoro-4-methyl-2-oxopentan-3-yl]propanamide;
(2S or 2R)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyrazin-2-ylpropanamide;
(2R or 2S)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyrazin-2-ylpropanamide;
(2S or 2R)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyridin-2-ylpropanamide;
(2R or 2S)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyridin-3-ylpropanamide;
(2S or 2R)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyridin-3-ylpropanamide;
(2R or 2S)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyridin-3-ylpropanamide;
(2S or 2R)-(3,5-Dichlorophenoxy)-N-[(1S)-1-(4-methoxyphenyl)-2-oxo-2-[[(3S)-1,1,1-trifluoro-4-methyl-2-oxopentan-3-yl]amino]ethyl]-3-pyridin-2-ylpropanamide;
(2R or 2S)-(3,5-Dichlorophenoxy)-N-[(1 S)-1-(4-methoxyphenyl)-2-oxo-2-[[(3S)-1,1,1-trifluoro-4-methyl-2-oxopentan-3-yl]amino]ethyl]-3-pyridin-2-ylpropanamide;
(2S or 2R)-(3,5-Dichlorophenoxy)-N—((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide;
(2R or 2S)-(3,5-Dichlorophenoxy)-N—((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide;
(S)-2-(2-(3-Cyanophenoxy)acetamido)-2-(4-methoxyphenyl)-N—((S)-1,1,1-trifluoro-4-methyl-2-oxopentan-3-yl)acetamide;
and pharmaceutically acceptable salts thereof.

Further particular examples of compounds of formula (I) as described herein are selected from
(2S)-2-[[(3R/S)-(3-Chlorophenyl)-3-phenylpropanoyl]amino]-3-phenyl-N-[(3S)-1,1,1-trifluoro-4-methyl-2-oxopentan-3-yl]propanamide;
(2S)-3-(4-Chlorophenyl)-2-[[2-(3,5-dichlorophenoxy)acetyl]amino]-N-[(3S)-1,1,1-trifluoro-4-methyl-2-oxopentan-3-yl]propanamide;
(E)-3-(3,4-Dichlorophenyl)-N-[(1S and 1R)-2-oxo-1-phenyl-2-[[(3S)-1,1,1-trifluoro-4-methyl-2-oxopentan-3-yl]amino]ethyl]prop-2-enamide;
(2S and 2R)-2-[[2-(3,5-Dichlorophenoxy)acetyl]amino]-2-phenyl-N-[(3S)-1,1,1-trifluoro-4-methyl-2-oxopentan-3-yl]acetamide;
(2S and 2R)-2-[[(2R/S)-(3,5-Dichlorophenoxy)-2-phenyl acetyl]amino]-2-phenyl-N-[(3S)-1,1,1-trifluoro-4-methyl-2-oxopentan-3-yl]acetamide;
3-(3,4-Dichlorophenyl)-N-[(1S or 1R)-1-(3-methoxyphenyl)-2-oxo-2-[[(3S)-1,1,1-trifluoro-4-methyl-2-oxopentan-3-yl]amino]ethyl]propanamide;
and pharmaceutically acceptable salts thereof.

Also further particular examples of compounds of formula (I) as described herein are selected from
(2R)-2-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-phenylpropanamide;
(2S or 2R)-(3,5-Dichlorophenoxy)-N-[(1 S and 1R)-2-oxo-1-phenyl-2-[[(3S)-1,1,1-trifluoro-4-methyl-2-oxopentan-3-yl]amino]ethyl]-3-pyridin-2-ylpropanamide;
(2R or 2S)-(3,5-Dichlorophenoxy)-N-[(1 S)-1-(4-methoxyphenyl)-2-oxo-2-[[(3S)-1,1,1-trifluoro-4-methyl-2-oxopentan-3-yl]amino]ethyl]-3-pyridin-2-ylpropanamide;
(2S or 2R)-(3,5-Dichlorophenoxy)-N—((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

AcOH=acetic acid, BOC=t-butyloxycarbonyl, BuLi=butyllithium, CDI=1,1-carbonyldiimidazole, DCM=dichloromethane, DBU=2,3,4,6,7,8,9,10-octahydropyrimido[1,2-a]azepine, DCE=1,2-dichloroethane, DIAD=diisopropyl-azodicarboxylate, DIBALH=di-i-butyl-aluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, Et$_2$O=diethylether, Et$_3$N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, IPC=in process control, LAH=lithium aluminium hydride, LDA=lithium diisopropylamide, LiBH$_4$=lithium borohydride, MeOH=methanol, NaBH$_3$CN, sodium cyanoborohydride, NaBH$_4$=sodium borohydride, NaI=sodium iodide, PG=protecting group, Red-Al=sodium bis(2-methoxyethoxy) aluminium hydride, RT=room temperature, TBDMSCl=t-butyldimethylsilyl chloride, TBTU=O-benzotriazol-1-yl-N,N,N',N'-tetramethyl-uronium tetrafluoroborate, TFA=trifluoroacetic acid, THF=tetrahydrofuran, quant=quantitative.

Amide coupling of N-protected-α-amino acid compounds 1 (scheme 1), such as BOC-L-phenyl alanine, with derivatives 2 can be accomplished by using one of the well-known coupling reagents such as TBTU, HATU, EDCI/HOBT, etc. and a base like Huenig's base or TEA in a solvent like N,N-dimethylformamide preferably between 0° C. and room temperature to give compounds 3 (step a). Subsequent deprotection under appropriate conditions, depending on the nature of the protecting group PG (step b), gives compounds 4 (e.g. acidic conditions such as treatment with 4M HCl in dioxane in a solvent like MeOH or treatment with TFA in DCM around room temperature can be used for removal of a BOC protecting group, catalytic hydrogenation conditions using suitable catalysts such as Pd/C, Pd(OH)$_2$ in a solvent like MeOH, EtOH or AcOEt around room temperature can be used for removal of a CBz protecting group, treatment with a mild base such as piperidine in a solvent like DCM around room temperature can be used for removal of a Fmoc protecting group, etc.). Reaction of compounds 4 with the appropriate carboxylic acid derivatives 5 (for the synthesis of specific examples of 5, see schemes 5, 6, 7, 8, 9 and 10), activated by one of the various coupling reagents such as TBTU, HATU, EDCI/HOBT, etc. and a base like Huenig's base or TEA in a solvent like N,N-dimethylformamide preferably between 0° C. and room temperature gives compounds 6 (step c). Oxidation of compounds 6 under suitable conditions such as Swern's conditions or by an appropriate oxidizing agent such as Dess-Martin Periodinane in a solvent like DCM between 0° C. and room temperature gives the final products I (step d).

$ZnCl_2$, in a solvent like MeOH, EtOH, IPA, tBuOH, THF, DMF, preferably in tert-butyl methyl ether around room temperature, followed by alkaline hydrolysis with a base, such as aqueous or non aqueous sodium, potassium or cesium carbonate, sodium or potassium hydroxyde, in a solvent like MeOH, EtOH and water around room temperature, gives compounds 54 (step c). Finally, deprotection under appropriate conditions, depending on the nature of the protecting group PG (step d), gives compounds 55 (e.g. acidic conditions such as treatment with 4M HCl in dioxane

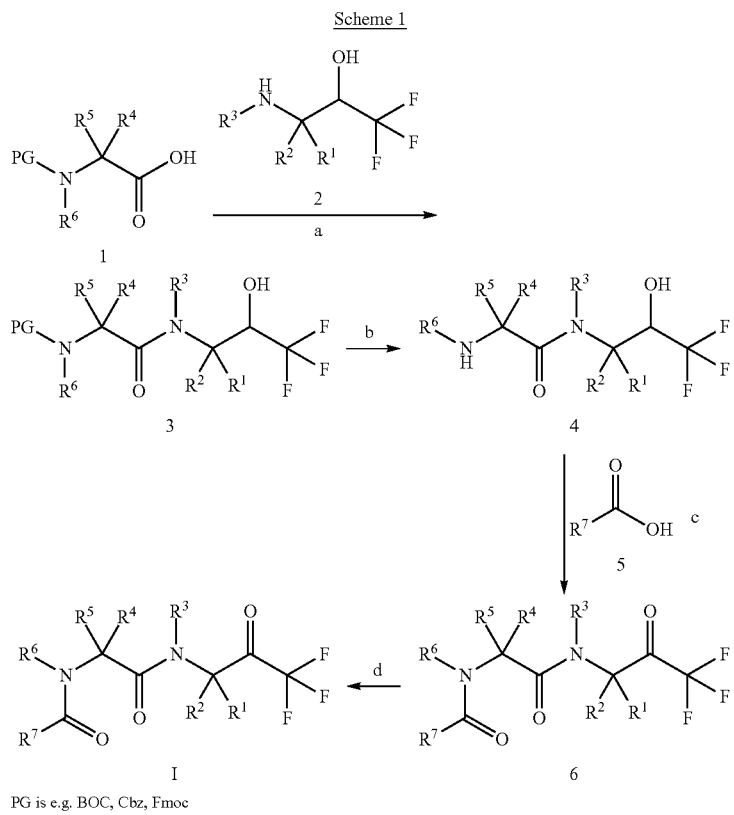

Scheme 1

PG is e.g. BOC, Cbz, Fmoc

Compounds 2 can be prepared by a variety of conditions, which may be exemplified by the general synthetic procedure below (scheme 4). Known N-protected-oxazolidin-5-one derivatives 52, preferably with fully defined stereochemistry, can be prepared by formylation of the corresponding enantiopure N-protected-α-amino acid derivatives 51, such as CBz-L-Valine, with paraformaldehyde in presence of Lewis acid catalysts, such as $ZnCl_2$, $AlCl_3$, $BF_3$ or preferably in presence of Brönstedt acid catalysts, such as pTsOH, CSA, AcOH, $H_2SO_4$, in a solvent like toluene, and in a temperature range preferably between 75° C. and about 90° C. (step a). Subsequent nucleophilic addition of a trifluoromethylating reagent, such as trifluoromethyltrimethylsilane (Ruppert's reagent), in the presence of a catalytic amount of a fluoride source such as TBAF or CsF, in a solvent like THF, and in a temperature range preferably between 0° C. and about 10° C., followed by deprotection of the TMS group by treatment in MeOH, gives compounds 53 with preferred stereochemistry as shown if $R^2$=H (step b). Stereoselective reduction of compounds 53 using suitable reducing agents such as $NaBH_4$, $LiBH_4$, $LiBHEt_3$, DIBALH, $NaBH_4$—$CeCl_3$ preferably $NaBH_4$— in a solvent like MeOH or treatment with TFA in DCM around room temperature can be used for removal of a BOC protecting group, catalytic hydrogenation conditions using suitable catalysts such as Pd/C, $Pd(OH)_2$ in a solvent like MeOH, EtOH or AcOEt around room temperature can be used for removal of a CBz protecting group, treatment with a mild base such as piperidine in a solvent like DCM around room temperature can be used for removal of a Fmoc protecting group). Alternatively, the hydroxy function of N-protected-α-amino trifluoromethyl alcohol derivatives 54 can be protected with a suitable protecting group, such as MOM, MEM, PMB or preferably THP using the appropriate conditions known by the person skilled in the art to give compounds 56 (step e). Subsequent N-alkylation by treatment of compounds 56 with an appropriate base, such as NaH, KH, NaHMDS, LiHMDS, LDA, in a solvent like THF, dioxane, DMF, in a temperature range between −78° C. and 0° C., followed by addition of alkyl or cycloalkyl halides, such as MeI, EtI, iPrI, CyPrI, etc., gives compounds 57 (step f). Finally, removal of both protecting groups PG and PG' under appropriate conditions, depending on the nature of the protecting group (step g), gives compounds 2 (e.g. acidic conditions such as treatment with 4M HCl in dioxane in a solvent like MeOH around room temperature can be used for removal of a BOC, MOM, MEM or THP protecting groups, catalytic hydrogenation conditions using suitable catalysts such as Pd/C, Pd(OH)$_2$ in a solvent like MeOH, EtOH or AcOEt around room temperature can be used for removal of CBz or PMB protecting groups).

between room temperature and the boiling point of the solvents used, potentially under pressure or using heterogeneous conditions such as Pd/C, in a solvent like MeOH, EtOH, or AcOEt around room temperature and under atmospheric pressure, gives alpha-phenyl-substituted phenylpropanoic acid derivatives 103 (step b).

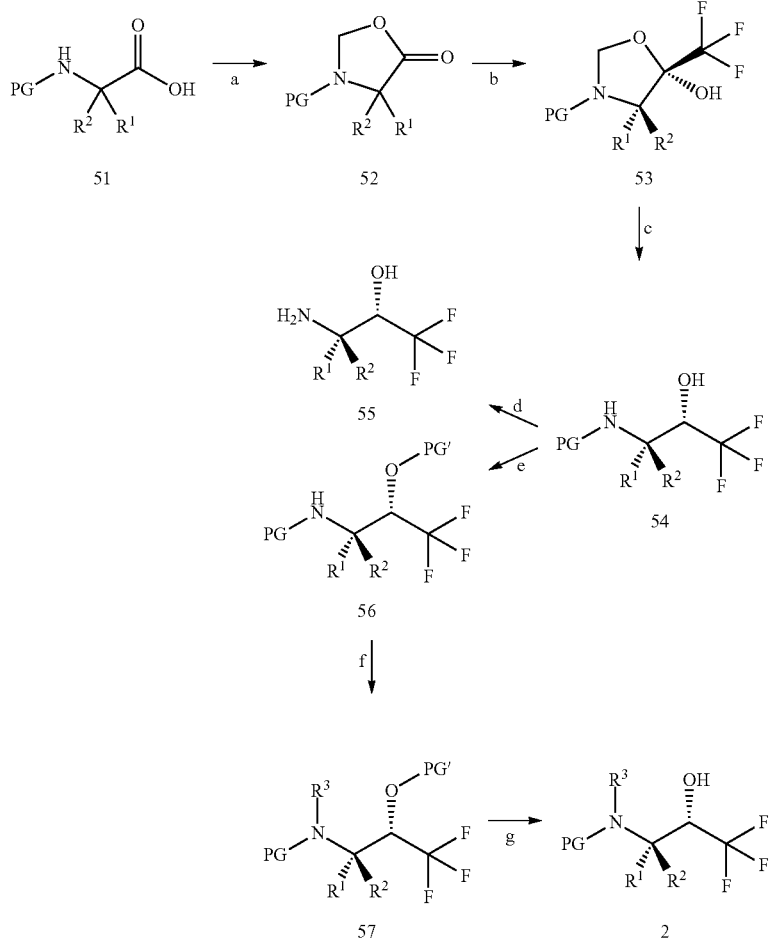

PG is e.g. BOC, Cbz, Fmoc
PG' is e.g. MOM, MEM, Cbz, THP

In case the carboxylic acid derivatives 5 are from the family of alpha-phenyl-substituted phenylpropanoic acid derivatives 103, these intermediates can be prepared according to the Perkin conditions, which may be exemplified by the general synthetic procedure below (scheme 5). The phenyl acetic acid derivatives 100 react with aromatic aldehyde derivatives 101 in the presence of a weak base, like the sodium or potassium salt of the acid, TEA or Huenig's base, in a solvent like acetic acid or acetic anhydride, and in temperature range between 80° C. and 140° C., preferably around the boiling point of the solvents used, to give preferentially alpha-phenylcinnamic acid stereoisomers in which the phenyl groups are in a cis relationship 102 (step a). Subsequent, catalytic hydrogenation using homogeneous conditions such as Wilkinson's catalyst, in a solvent like MeOH, EtOH or AcOEt, in a temperature range preferably

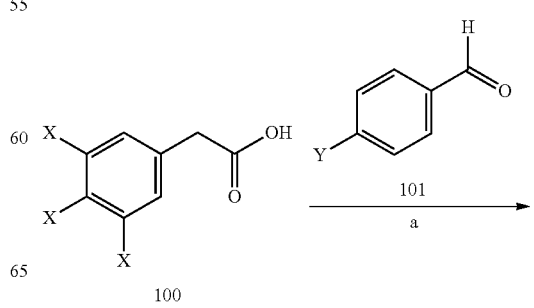

-continued

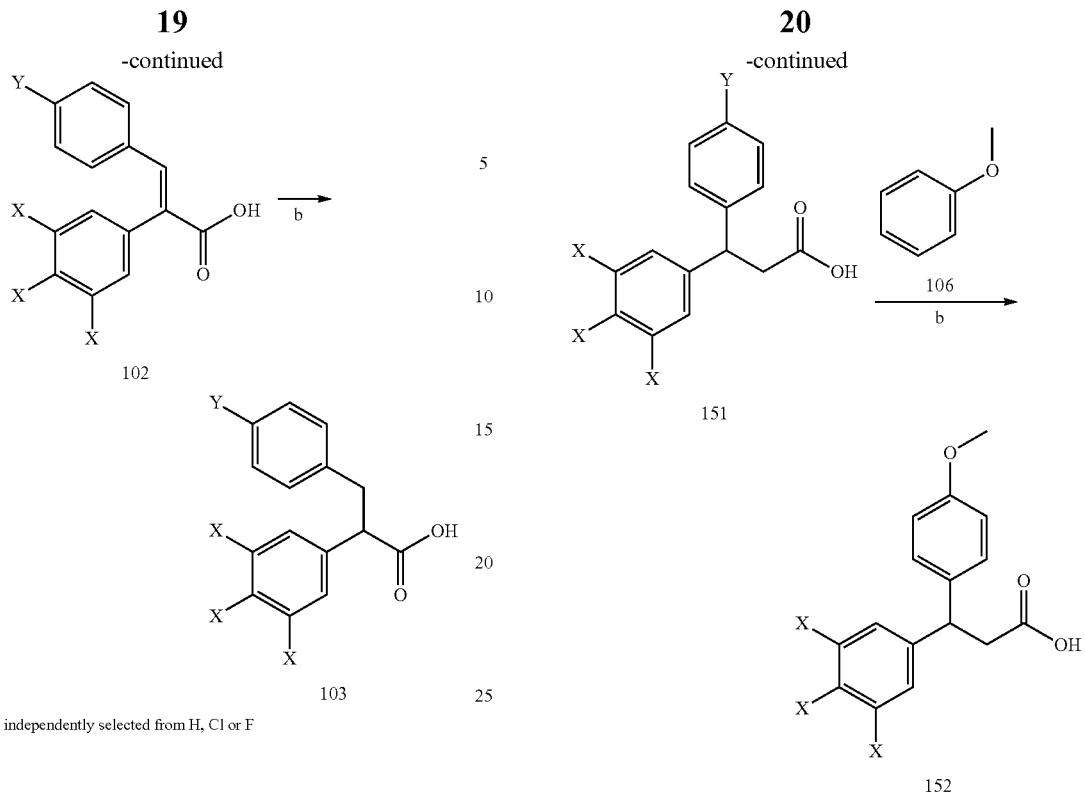

X substituents are independently selected from H, Cl or F
Y is H or OMe

In case the carboxylic acid derivatives 5 are from the family of beta-phenyl substituted phenylpropanoic acid derivatives 151, 152, 153, these intermediates can be prepared by a variety of conditions, which may be exemplified by the general synthetic procedures below, named here "Grignard route" and the "Friedel-craft route" (scheme 6) and the "Michael condensation route" (scheme 7). The person skilled in the art will appreciate that compounds 151, 152, 153 can also be prepared by variations of these procedures.

The phenyl cinnamic acid derivatives 104 react with phenyl magnesium bromide derivatives 105 optionally in presence of catalytic amount of CuI, in a solvent like diethylether or THF, and in temperature range preferably between −10° C. and 0° C., to give beta-phenylsubstituted phenylpropanoic acid compounds 151 (step a). Alternatively, the phenyl cinnamic acid derivatives 104 react with anisol 106 in presence of a Brönstedt acid, such as para toluene sulfonic acid, in temperature range between about 50° C. and 150° C., preferably around 80° C. to give beta-phenylsubstituted methoxyphenylpropanoic acid derivatives 152 (step b).

Alternatively, aromatic aldehyde derivatives 107 (scheme 7) are condensed with ethyl-2-cyanoacetate 108 in presence of a base such as sodium or potassium hydroxide pellets, in a solvent like EtOH, and around room temperature, to give preferentially the cis cyanophenylcinnamic esters 109. Subsequent Grignard reaction with phenyl magnesium bromide derivatives 105 optionally in presence of catalytic amount of CuI, in a solvent like diethylether or THF, and in temperature range preferably between −10° C. and 0° C., gives compounds 110 (step b). Finally, hydrolysis and decarboxylation under acidic conditions using a mixture of acetic acid and sulfuric acid in water, in a temperature range between 100° C. and 120° C., preferably around reflux, gives the beta-phenylsubstituted phenylpropanoic acid derivatives 151 (step c).

Scheme 6

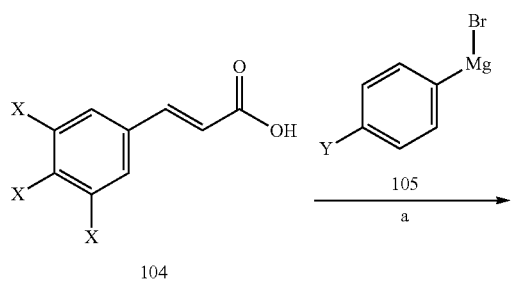

Scheme 7

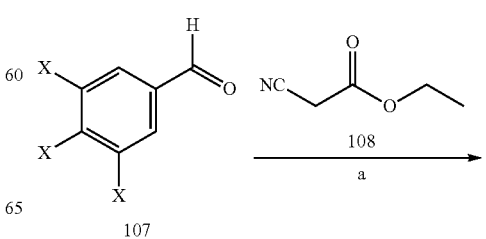

-continued

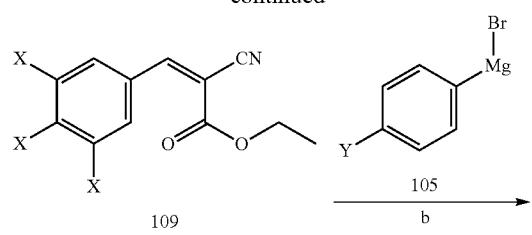

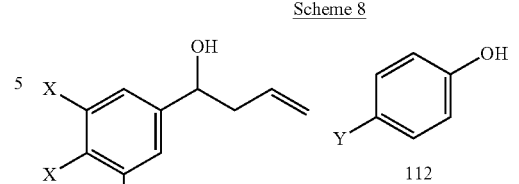

Scheme 8

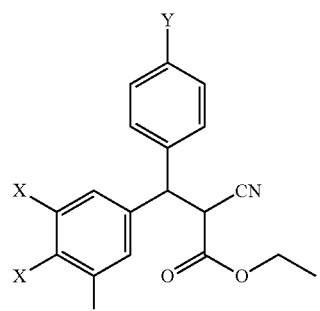

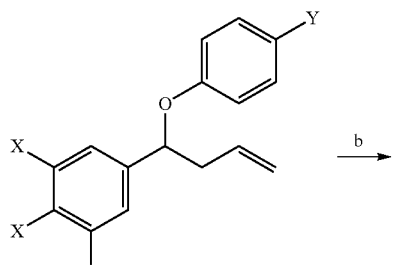

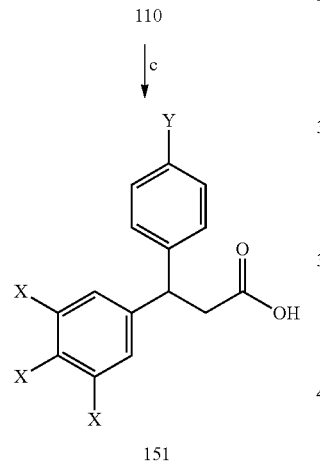

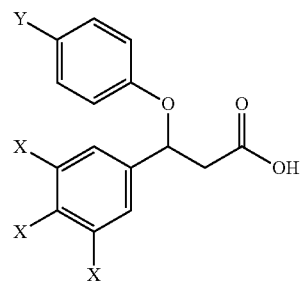

X substituents are independently selected from H, Cl or F
Y is H or OMe

151

X substituents are independently selected from H, Cl or F
Y is H or OMe

153

In case the carboxylic acid derivatives 5 are from the family of beta-phenoxy phenylpropanoic acid derivatives 153, these intermediates can be prepared by a variety of conditions, which may be exemplified by the general synthetic procedure below (scheme 8). Mitsunobu reaction between phenyl buten-ol derivatives 111 and suitable phenol derivatives 112, such as 4-methoxyphenol, using e.g. DIAD, triphenylphosphine, in a solvent like THF and in a temperature range between 0° C. and room temperature gives ether derivatives 113 (step a). Alkene oxidation using e.g. a mixture of sodium periodate and potassium permanganate in presence of a base such as potassium carbonate, in a solvent mixture like tBuOH/water, and in a temperature range preferably between 0° C. and room temperature finally gives suitable beta substituted phenoxy phenylpropanoic acid derivatives 153 (step b).

In case the carboxylic acid derivatives 5 belong to the family of alpha-aryloxy substituted phenyl or cyclohexyl propanoic acid derivatives 154, these intermediates can be prepared by a variety of conditions, which may be exemplified by the general synthetic procedure below (scheme 9). Mitsunobu reaction between alpha-hydroxy substituted phenyl or alpha-hydroxy substituted cyclohexyl propanoate derivatives 114 and suitable phenol derivatives 115, such as 3,5-dichlorophenol, using e.g. DIAD, triphenylphosphine, in a solvent like THF and in a temperature range between 0° C. and room temperature gives ether derivatives 116 (step a). Alkaline hydrolysis of the ester functional group with an appropriate base, such as aqueous or non aqueous sodium, potassium or cesium carbonate, sodium or potassium hydroxide, preferably lithium hydroxide, in a solvent like MeOH, EtOH, THF, dioxane, preferably in a mixture of THF/water and in a temperature range between room temperature and the reflux temperature of the solvents, gives the alpha-phenoxy substituted phenyl or cyclohexyl propanoic acid derivatives 154 (step b).

Scheme 9

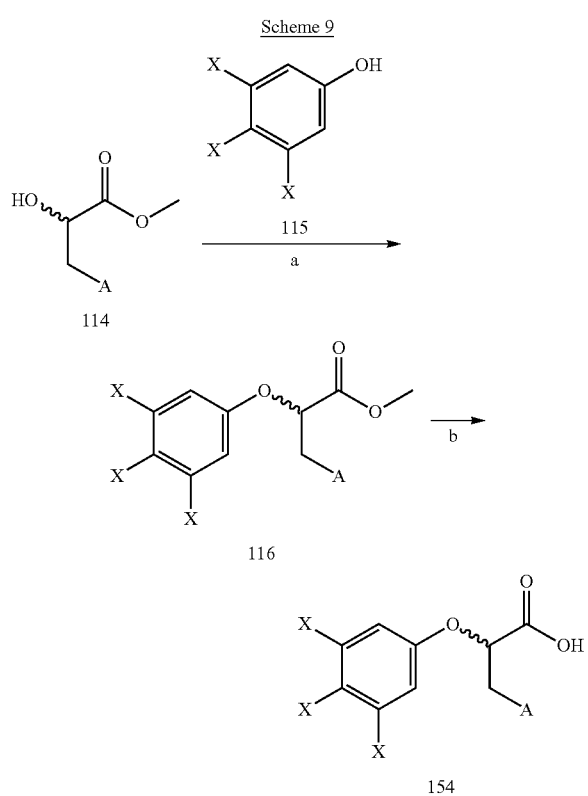

A is phenyl, substituted phenyl, cycloalkyl or substituted cycloalkyl
X substituents are independently selected from H, Cl or F In case the carboxylic acid derivatives 5 are from the family of alpha-phenoxy aryl or heteroaryl propanoic acid derivatives 155, these intermediates can be prepared by a variety of conditions, which may be exemplified by the general synthetic procedure below (scheme 10). Darzens reaction between a suitable aryl or heteroaryl aldehyde 117 and alpha haloester compounds 115, such as ethyl 2-chloroacetate, using a strong base such as NaH, KH, NaOEt, LiHMDS, LDA, preferably NaHMDS, in a solvent like THF and in a temperature range between −78° C. to room temperature gives cis and trans α,β-epoxy ester derivatives 118 (step a). Selective epoxide hydrogenolysis using an appropriate catalyst, such as Pd/C, Pd/Fe$_2$O$_3$, preferably Pd(OH)$_2$ in a solvent like AcOEt around room temperature gives the alpha-hydroxy aryl or heteroaryl propanoate derivatives 119 (step b). Subsequent Mitsunobu reaction by treatment of compounds 119 with a suitable phenol derivatives 115, such as 3,5-dichlorophenol, using e.g. DIAD, triphenylphosphine, in a solvent like THF and in a temperature range between 0° C. and room temperature gives ether derivatives 120 (step c). Alkaline hydrolysis of the ester functional group with an appropriate base, such as aqueous or non aqueous sodium, potassium or cesium carbonate, sodium or potassium hydroxide, preferably lithium hydroxide, in a solvent like MeOH, EtOH, THF, dioxane, preferably in a mixture of THF/water in a temperature range between room temperature and the reflux temperature of the solvents finally gives the alpha-phenoxy aryl or heteroaryl propanoic acid derivatives 155 (step d).

Scheme 10

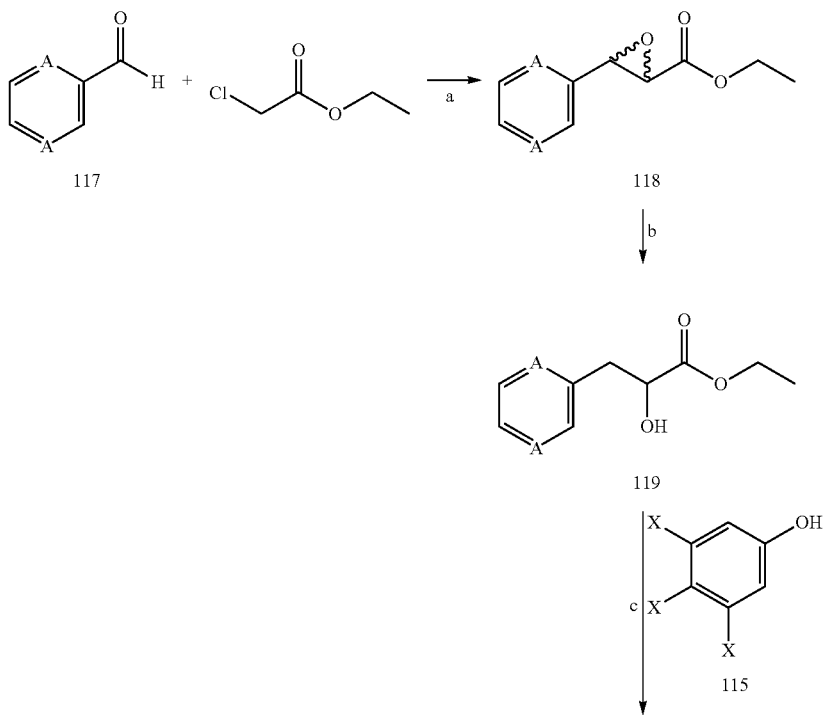

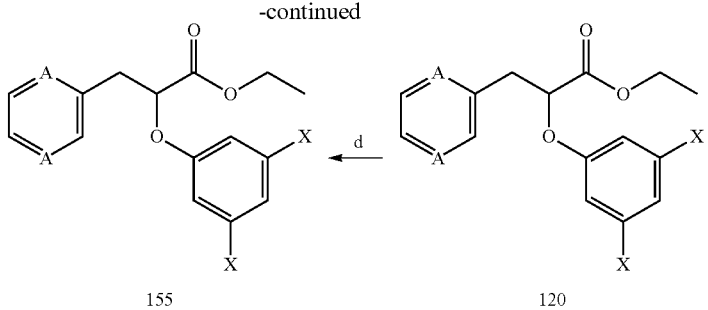

155 ← d ─ 120

A substituents are independently selected from C or N
X substituents are independently selected from H, Cl, or F Also an embodiment of the present invention is a process to prepare a compound of formula (I) as defined above comprising the reaction of a compound of formula (II) in oxidative conditions;

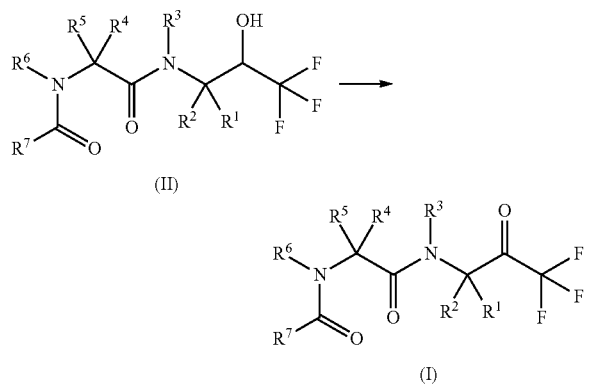

wherein $R^1$, $R^2$, $R^3$, $R^4$, $R^5$, $R^6$ and $R^7$ are as defined above.

In particular, in the presence of 1,1,1-Triacetoxy-1,1-dihydro-1,2-benziodoxol-3(1H)-one (Dess-Martin periodane), in a solvent like DCM between 0° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of ocular diseases, in particular HtrA1-mediated ocular diseases, more particularly wet or dry age-related macular degeneration, geographic atrophy, diabetic retinopathy, retinopathy of prematurity or polypoidal choroidal vasculopathy.

In a particular embodiment, the compounds of formula (I) or their pharmaceutically acceptable salts and esters can be used for the treatment or prophylaxis of wet or dry age-related macular degeneration, geographic atrophy, diabetic retinopathy, retinopathy of prematurity or polypoidal choroidal vasculopathy.

The present invention also relates to the use of a compound according to formula (I) as described herein for the preparation of a medicament for the treatment or prophylaxis of wet or dry age-related macular degeneration, geographic atrophy, diabetic retinopathy, retinopathy of prematurity and polypoidal choroidal vasculopathy.

Also an object of the invention is a method for the treatment or prophylaxis of wet or dry age-related macular degeneration, geographic atrophy, diabetic retinopathy, retinopathy of prematurity and polypoidal choroidal vasculopathy, which method comprises administering an effective amount of a compound according to formula (I) as described herein.

Also an embodiment of the present invention are compounds of formula (I) as described herein, when manufactured according to any one of the described processes.

Assay Procedures

Protein Purification for Use in Enzymatic Assays

Human HtrA1 protein comprising the catalytic and the PDZ domain from amino acid Asp161 up to Pro480 of was expressed in BL21(DE3) cells as an N-terminal fusion protein with a 6×His-SUMO tag. The transformed cells were grown in LB medium at 37° C. until the optical density at 600 nm was between 0.6 and 0.8. Then, the temperature was decreased to 18° C. and the recombinant protein production induced by adding IPTG to a final concentration of 250 mM. Fermentation was performed over night at 18° C.

The protein was purified to homogeneity following a four-step procedure. 40 g of cells were suspended in 50 mM HEPES pH 7.8, 250 mM NaCl, 10 mM MgCl2, 0.35% CHAPS, 10% glycerol containing 20 tabs per liter of EDTA-free cOmplete Protease Inhibitor (Roche) as well as 30 mg/l DNAse and Rnase. The cells were broken by a single passage through a homogenizer at 750 bar and then centrifuged at 20'000×g for 30 minutes. The clear supernatant was applied on a triple 5 ml HisTrap column (GE Healthcare) equilibrated in 50 mM HEPES pH 7.8, 500 mM NaCl, 0.35% CHAPS, 10% glycerol. After washing with stepwise increasing concentrations of imidazole (20 mM, 40 mM, 50 mM) HtrA1 fusion protein was eluted within a linear gradient from 10 to 100% of the same buffer containing 500 mM imidazole. HtrA1 containing fractions were pooled, concentrated and then applied to a Superdex 5200 prep grade (XK26/100—GE Healthcare) column equilibrated in 50 mM ethanolamine pH 9.6, 500 mM NaCl, 0.35% CHAPS, 10% glycerol, 0.02% sodium azide. In order to cleave the SUMO fusion protein and to release active HtrA1, the pooled fractions from the size exclusion chromatography were blended with SUMO protease (Life Technologies) and incubated ca. 20 hours at RT. HtrA1 was isolated out of the reaction solution by chromatography on a Superdex S200 prep grade (XK26/100—GE Healthcare) column equilibrated 50 mM ethanolamine pH 9.6, 500 mM NaCl, 0.35% CHAPS, 10% glycerol, 0.02% sodium azide. Fractions containing active HtrA1 were pooled and concentrated. Following the above strategy 150 mg of the HtrA1 (catalytical domain/PDZ construct) could be purified. As shown by RP-HPLC and SDS-PAGE, >98% pure protein was obtained.

HtrA1 Enzyme Inhibition Assay

Enzyme activity is measured by observing the increase in fluorescence intensity caused by cleavage of a peptide substrate containing a fluorophore, whose emission is quenched in the intact peptide.

Assay buffer: 500 mM Tris pH 8.0, 200 mM NaCl, 0.025% CHAPS, 0.005% BSG

Enzyme: human HtrA1 Cat-PDZ, final concentration 1 nM

Substrate: Mca-Ile-Arg-Arg-Val-Ser-Tyr-Ser-Phe-Lys (Dnp)-Lys, final concentration 500 nM (from Innovagen Cat: SP-5076-1, Lot: 89584.02)

Mca=(7-Methoxycoumarin-4-yl)acetyl
Dnp=2,4-Dinitrophenyl
Final volume: 51 µl
Excitation 320 nm, emission 390 nm After a pre-incubation of the HtrA1 protease for 30 min with compounds, substrate is added to the wells and initial RFU is measured. Upon incubation for 2 hours at RT, the enzymatic activity cleaved the substrate releasing fluorescent Mca-peptide conjugate and the final RFU value is measured. The presence of inhibitors leads to a decreased final RFU. For the analysis ΔRFU is calculated as $RFU_{end} - RFU_{start}$ and then percent inhibition is calculated with the following formula:

$$PCT\_Inhibition = 100 - 100*(\Delta RFU_{compound} - \Delta RFU_{blank})/(\Delta RFU_{negctrl} - \Delta RFU_{blank})$$

where
neg.ctrl is protease with substrate and DMSO
blank is as neg. ctrl without protease
compound is as neg. ctrl with test compounds at desired concentration
The $IC_{50}$ is determined using a 4-point Hill-fit equation where
x=concentration of test compound
A=extrapolated value of the curve at effector concentration equals 0
B=extrapolated value of the curve at effector concentration equals infinite
C=concentration at the inflection point of the sigmoidal curve ($IC_{50}$)
D=Hill coefficient of slope at the inflection point of the fitted curve $$Y(x) = A + \frac{B - A}{1 + \left(\frac{C}{x}\right)^D}$$

As a counter screen the compounds are added to the protease-substrate reaction mix only after 2 h incubation, when all the substrate is turned over, to identify auto-fluorescent or absorbing compounds giving false positive hits.

| Example | IC50 (µM) |
|---|---|
| 1 | 0.1 |
| 2 | 0.193 |
| 3 | 0.11 |
| 4 | 0.037 |
| 5 | 1.1 |
| 6 | 0.06 |
| 7 | 0.21 |
| 8 | 0.125 |
| 9 | 0.08 |
| 10 | 0.135 |
| 11 | 0.055 |
| 12 | 0.035 |
| 13 | 1.555 |
| 14 | 0.058 |
| 15 | 0.225 |
| 16 | 0.09 |
| 17 | 0.07 |
| 18 | 0.09 |
| 19 | 0.015 |
| 20 | 0.14 |
| 21 | 0.045 |
| 22 | 0.06 |
| 23 | 0.015 |
| 24 | 0.01 |
| 25 | 3.1 |
| 26 | 2.54 |
| 27 | 0.77 |
| 28 | 0.009 |
| 29 | 0.02 |
| 30 | 0.02 |
| 31 | 0.065 |
| 32 | 0.05 |
| 33 | 0.025 |
| 34 | 0.07 |
| 35 | 0.035 |
| 36 | 0.01 |
| 37 | 0.13 |
| 38 | 0.03 |
| 39 | 0.08 |
| 40 | 0.06 |
| 41 | 0.21 |
| 42 | 3.45 |
| 43 | 0.94 |
| 44 | 0.13 |
| 45 | 0.07 |
| 46 | 0.006 |
| 48 | 0.01 |
| 50 | 0.01 |
| 52 | 0.023 |
| 54 | 0.000976 |
| 55 | 0.00118 |
| 56 | 0.0151 |
| 57 | 0.0778 |
| 58 | 0.0602 |
| 59 | 0.059 |
| 60 | 0.65 |
| 61 | 0.00331 |
| 62 | 0.218 |
| 63 | 0.004525 |
| 64 | 0.00447 |
| 65 | 0.4945 |
| 66 | 0.0106 |
| 67 | 0.0566 |
| 68 | 0.0505 |
| 69 | 0.00607 |
| 70 | 0.04855 |
| 71 | 0.0101 |
| 72 | 0.0589 |
| 73 | 0.0373 |
| 74 | 0.00428 |
| 75 | 0.002885 |
| 76 | 0.0483 |
| 77 | 0.345 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500

μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations; lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg, can be administered either by single dose per day or per week, or by multiple doses (2 to 4) per day, or by multiple doses per week. In case of parenteral application, such as intramuscularly, intravenously, or intraocularly, the formulation can contain 0.001% to 15% by weight of medicament and the required dose, which can be between 0.01 and 25 mg, can be administered either by single dose per day, per week or per month, or by multiple doses (2 to 4) per day, or by multiple doses per week or per month. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated Intermediate A-1

(2S)-2-[3-(3,4-Dichlorophenyl)propanoylamino]-3-phenyl-N-[(1S,2S)-3,3,3-trifluoro-2-hydroxy-1-isopropyl-propyl]propanamide

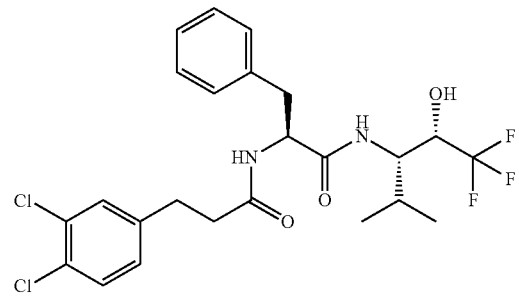 [SMILES: CC(C)[C@H](NC(=O)[C@H](Cc1ccccc1)NC(=O)CCc1ccc(Cl)c(Cl)c1)[C@H](O)C(F)(F)F]

[A] tert-Butyl N-[(1S)-1-benzyl-2-oxo-2-[[(1S,2S)-3,3,3-trifluoro-2-hydroxy-1-isopropyl-propyl]amino]ethyl]carbamate

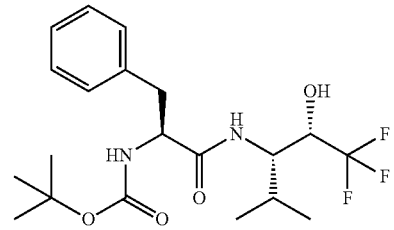 [SMILES: CC(C)[C@H](NC(=O)[C@H](Cc1ccccc1)NC(=O)OC(C)(C)C)[C@H](O)C(F)(F)F]

In a round-bottomed flask, (2S,3S)-3-amino-1,1,1-trifluoro-4-methylpentan-2-ol×HCl (0.25 g, 1.2 mmol), (S)-2-(tert-butoxycarbonylamino)-3-phenylpropanoic acid (0.319 g, 1.2 mmol) and HATU (0.687 g, 1.81 mmol) were mixed in DMF (2 mL). Then, Hünig's base (0.63 mL, 3.61 mmol) was added and the reaction mixture was stirred at room temperature overnight. The mixture was diluted with EtOAc, poured into a 1N aqueous HCl solution (10 mL) and the aqueous layer was extracted with EtOAc (20 mL). Combined organics were washed with a sat. $NaHCO_3$ solution (10 mL), then brine before being dried over $Na_2SO_4$, filtered and concentrated in vacuo. The residue was triturated with diisopropylether, the solid precipitate was filtered off and the filtrate was evaporated to dryness. The resulting material was then purified by silica gel flash chromatography eluting with a 0 to 60% EtOAc-heptane gradient to give the title compound (0.33 g, 65%) as a colorless solid. MS: 419.3 (M+H$^+$).

[B] (2S)-2-Amino-3-phenyl-N-[(1S,2S)-3,3,3-trifluoro-2-hydroxy-1-isopropyl-propyl]propanamide hydrochloride

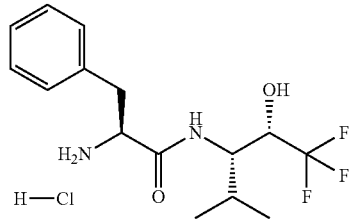

To a solution of tert-butyl N-[(1S)-1-benzyl-2-oxo-2-[[(1S,2S)-3,3,3-trifluoro-2-hydroxy-1-isopropyl-propyl]amino]ethyl]carbamate (0.325 g, 0.777 mmol) in MeOH (5 mL) was added 4M HCl in dioxane solution (0.97 mL, 3.88 mmol) and the reaction mixture was stirred at room temperature overnight. The mixture was evaporated to dryness and the residue was triturated with diisopropylether. The solid precipitate was filtered off and further dried under the high vacuum to give the title compound (0.3 g, 98%) as a colorless solid as the HCl salt. MS: 319.2 (M+H$^+$).

[C] (2S)-2-[3-(3,4-Dichlorophenyl)propanoylamino]-3-phenyl-N-[(1S,2S)-3,3,3-trifluoro-2-hydroxy-1-isopropyl-propyl]propanamide

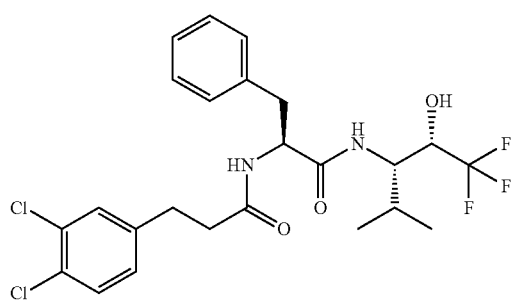 [SMILES: CC(C)[C@H](NC(=O)[C@H](Cc1ccccc1)NC(=O)CCc1ccc(Cl)c(Cl)c1)[C@H](O)C(F)(F)F]

In a round-bottomed flask, (2S)-2-amino-3-phenyl-N-[(1S,2S)-3,3,3-trifluoro-2-hydroxy-1-isopropyl-propyl]propanamide hydrochloride (0.05 g, 0.141 mmol), HATU (0.064 g, 0.169 mmol) and 3-(3,4-dichlorophenyl)propanoic acid (0.031 g, 0.141 mmol) were mixed in DMF (1 mL). Then Hünig's base (0.062 mL, 0.352 mmol) was added and the reaction mixture was stirred at room temperature for 4 h. The mixture was diluted with EtOAc, poured into a 1N aqueous HCl solution (5 mL) and the aqueous layer was extracted with EtOAc (10 mL). Combined organics were washed with a sat. NaHCO$_3$ solution (5 mL), then brine before being dried over Na$_2$SO$_4$, filtered and concentrated in vacuo. The residue was triturated in DCM, the solid precipitate was filtered off and further dried under the high vacuum to give the title compound (0.058 g, 79%) as a colorless solid. MS: 519.2 (M+H$^+$).

Intermediate B-1

3-(3-Chlorophenyl)-3-(4-methoxyphenoxy)propanoic acid

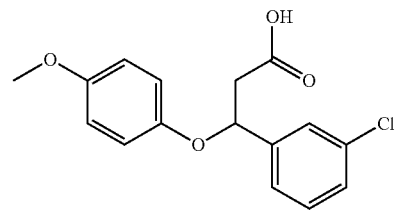 [SMILES: COc1ccc(OC(CC(=O)O)c2cccc(Cl)c2)cc1]

[A] 1-Chloro-3-[1-(4-methoxyphenoxy)but-3-enyl]benzene

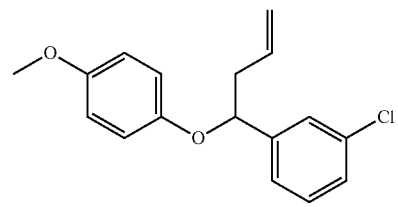 [SMILES: C=CCC(Oc1ccc(OC)cc1)c1cccc(Cl)c1]

A solution of DIAD (0.72 g, 3.56 mmol) in THF (4 mL) was added dropwise to a mixture of 1-(3-chlorophenyl)but-3-en-1-ol (0.5 g, 2.74 mmol), 4-methoxyphenol (0.408 g, 3.29 mmol) and triphenylphosphine (0.862 g, 3.29 mmol) in THF (8 mL) at 0° C. under Ar. The mixture was then stirred at room temperature for 6 h. The mixture was diluted with EtOAc, poured into water (25 mL) and the aqueous layer was extracted with EtOAc (2×50 mL). Combined organics were washed with brine, dried over Na$_2$SO$_4$, filtered and evaporated to dryness. The yellow oily residue was taken up in diisopropylether and the white solid precipitate was filtered off. The mother liquors were evaporated to dryness and the resulting material purified by silica gel flash chromatography eluting with a 0 to 20% EtOAc-heptane gradient to give the title compound (0.523 g, 66%) as a colorless oil. MS: 287.3 (M–H$^-$).

[B] 3-(3-Chlorophenyl)-3-(4-methoxyphenoxy)propanoic acid

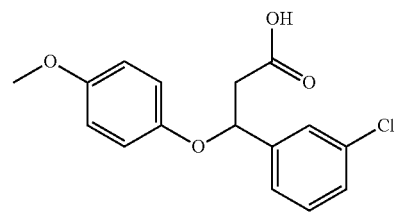 [SMILES: COc1ccc(OC(CC(=O)O)c2cccc(Cl)c2)cc1]

A solution of sodium periodate (4.06 g, 19 mmol) and potassium permanganate (0.178 g, 1.13 mmol) in water (74 mL) was treated with a solution of K$_2$CO$_3$ (3.75 g, 27.1 mmol) in water (9 mL), and then with tBuOH (5 mL). A solution of 1-chloro-3-[1-(4-methoxyphenoxy)but-3-enyl] benzene (0.522 g, 1.81 mmol) in tBuOH (22 mL) was then slowly added to the mixture cooled to 0° C. with an ice bath and the reaction mixture was stirred at room temperature overnight. The resulting suspension was treated with ethylene glycol (2.02 mL, 36.1 mmol), stirred for 5 h, then cooled to 0° C. with an ice bath and slowly acidified to pH 2 with a 25% conc. HCl aqueous solution (10 mL). The unsoluble brown solid residue was filtered off and the aqueous solution was extracted with EtOAc (2×100 mL). Combined organics were washed with brine, dried over Na$_2$SO$_4$, filtered and evaporated to dryness. The resulting material was purified by silica gel flash chromatography eluting with a 0% to 40% EtOAc-heptane gradient to give the title compound (0.498 g, 85%) as a light brown oil. MS: 305.2 (M–H$^-$)

Intermediate B-2

3-(4-Chlorophenyl)-3-(4-methoxyphenoxy)propanoic acid

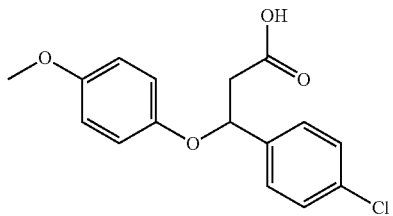 [SMILES: COc1ccc(OC(CC(=O)O)c2ccc(Cl)cc2)cc1]

In analogy to the procedure described for the preparation of intermediate B-1, 1-(4-chlorophenyl)but-3-en-1-ol has been reacted with 4-methoxyphenol, triphenylphosphine and DIAD under Mitsunobu coupling conditions (step [A]), followed by oxidation with a mixture of sodium periodate and potassium permanganate in presence of K$_2$CO$_3$ (step [B]) to give the title compound as a white solid. MS: 305.2 (M–H$^-$).

Intermediate B-3

3-(3,4-Dichlorophenyl)-3-(4-methoxyphenoxy)propanoic acid

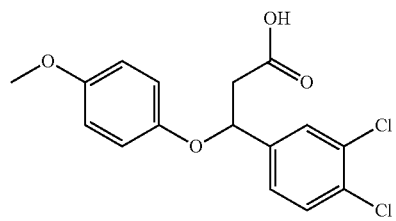 [SMILES: COc1ccc(OC(CC(=O)O)c2ccc(Cl)c(Cl)c2)cc1]

In analogy to the procedure described for the preparation of intermediate B-1, 1-(3,4-dichlorophenyl)but-3-en-1-ol has been reacted with 4-methoxyphenol, triphenylphosphine and DIAD under Mitsunobu coupling conditions (step [A]), followed by oxidation with a mixture of sodium periodate and potassium permanganate in presence of K$_2$CO$_3$ (step [B]) to give the title compound as a yellow oil. MS: 339.2 (M–H$^-$)

Intermediate B-4

3-(4-Chlorophenyl)-2-(4-methoxyphenyl)propanoic acid

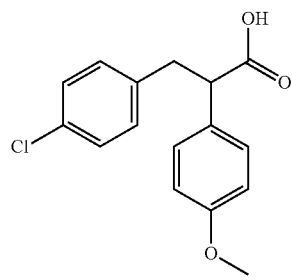 [SMILES: COc1ccc(C(Cc2ccc(Cl)cc2)C(=O)O)cc1]

[A] (E)-3-(4-Chlorophenyl)-2-(4-methoxyphenyl)prop-2-enoic acid

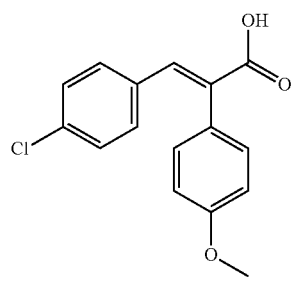 [SMILES: COc1ccc(/C(=C\c2ccc(Cl)cc2)C(=O)O)cc1]

4-Chlorobenzaldehyde (0.5 g, 3.56 mmol) and 2-(4-methoxyphenyl)acetic acid (0.598 g, 3.6 mmol) were dissolved in acetic anhydride (5 mL) and triethylamine (1 mL, 7.17 mmol) was slowly added to the stirring mixture at room temperature. The reaction mixture was then heated to reflux and stirred overnight. The mixture was quenched with water (5 mL) and was further refluxed for 1 hr. After cooling to room temperature, the solid precipitate was filtered off, washed with water and dried under high vacuum to give the title compound (0.740 g, 72%) as a yellow solid. MS: 289.2 (M+H$^+$).

[B] 3-(4-Chlorophenyl)-2-(4-methoxyphenyl)propanoic acid

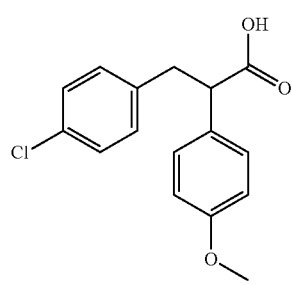 [SMILES: COc1ccc(C(Cc2ccc(Cl)cc2)C(=O)O)cc1]

To a stirred solution of (E)-3-(4-chlorophenyl)-2-(4-methoxyphenyl)prop-2-enoic acid (0.38 g, 1.32 mmol) in ethyl acetate (8 mL) was added Wilkinson's catalyst acid (0.08 g, 0.084 mmol). The flask was purged with argon before being purged with H₂ several times. The reaction mixture was stirred at 80° C. under 40 bar of H₂ for 8 h. The Wilkinson's catalyst was removed by filtration and the filtrate concentrated in vacuo. The residue was purified by reverse phase HPLC to give the title compound (0.107 g, 28%) as an off-white solid. MS: 289.2 (M–H⁻)

Intermediate B-5

3-(4-Chlorophenyl)-3-(4-methoxyphenoxy)propanoic acid

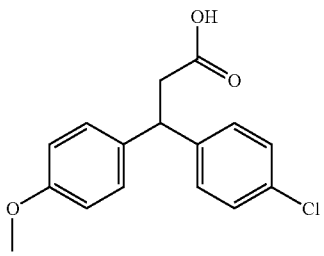 [SMILES: COc1ccc(C(CC(=O)O)c2ccc(Cl)cc2)cc1]

In a sealed tube, (E)-3-(4-chlorophenyl)acrylic acid (0.25 g, 1.37 mmol), anisole (0.163 g, 1.51 mmol) and 4-methylbenzenesulfonic acid hydrate (0.26 g, 1.37 mmol) were mixed and heated to 125° C. for 5 h. After cooling, the red solid was dissolved in EtOAc, poured into water (10 mL) and the aqueous layer was extracted with EtOAc (2×25 mL). Combined organics were washed with brine, dried over Na₂SO₄, filtered and evaporated. The residue was purified by silica gel flash chromatography, eluting with a 0 to 40% EtOAc-heptane gradient to give a 2/1 mixture of 3-(4-chlorophenyl)-3-(4-methoxyphenoxy)propanoic acid and 3-(4-chlorophenyl)-3-(2-methoxyphenoxy)propanoic acid. This material was then re-purified by HPLC chromatography (Reprosil Chiral NR column, gradient: 0-30% ethanol-heptane) to give the title compound (0.137 g, 34%) as a colorless solid. MS: 289.3 (M–H⁻) and its isomer (0.06, 15%) as a yellow solid. MS: 289.3 (M–H⁻).

Intermediate B-6

3-(3,4-Dichlorophenyl)-3-(4-methoxyphenoxy)propanoic acid

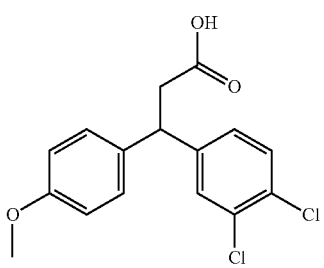 [SMILES: COc1ccc(C(CC(=O)O)c2ccc(Cl)c(Cl)c2)cc1]

In analogy to the procedure described for the preparation of intermediate B-5, (E)-3-(3,4-dichlorophenyl)acrylic acid has been reacted with anisole and 4-methylbenzenesulfonic acid hydrate under heating at 135° C. overnight to give the title compound as a red solid. MS: 323.2 (M–H⁻).

Intermediate B-7

3-Cyclohexyl-2-(3,5-dichlorophenoxy)propanoic acid

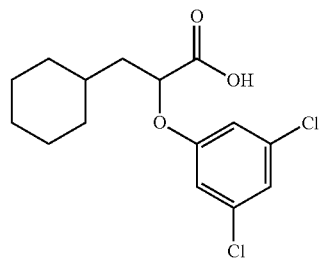 [SMILES: O=C(O)C(CC1CCCCC1)Oc1cc(Cl)cc(Cl)c1]

[A] Methyl 3-cyclohexyl-2-(3,5-dichlorophenoxy)propanoate

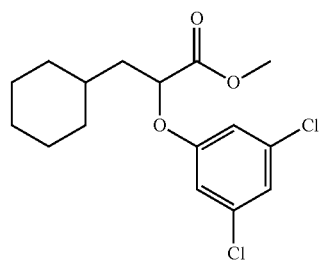 [SMILES: COC(=O)C(CC1CCCCC1)Oc1cc(Cl)cc(Cl)c1]

A solution of DIAD (0.375 g, 1.74 mmol) in THF (1 mL) was added dropwise to a mixture of methyl 3-cyclohexyl-2-hydroxypropanoate (0.25 g, 1.34 mmol), 3,5-dichlorophenol (0.263 g, 1.61 mmol) and triphenylphosphine (0.422 g, 1.61 mmol) in THF (1.5 mL) at 0° C. under Ar. The mixture was then stirred at room temperature for 20 h. The mixture was diluted with EtOAc, poured into water (7 mL) and the aqueous layer was extracted with EtOAc (2×20 mL). Combined organics were washed with brine, dried over Na₂SO₄, filtered and evaporated to dryness. The yellow oily residue was taken up in heptane and the white solid precipitate was filtered off. The mother liquors were evaporated to dryness and the resulting material purified by silica gel flash chromatography eluting with a 0 to 20% EtOAc-heptane gradient to give the title compound (0.388 g, 85%) as a colorless solid.

[B] 3-Cyclohexyl-2-(3,5-dichlorophenoxy)propanoic acid

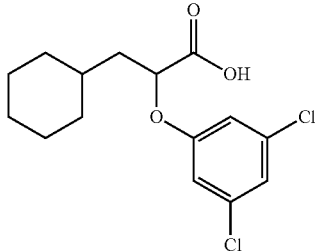 [SMILES: O=C(O)C(CC1CCCCC1)Oc1cc(Cl)cc(Cl)c1]

To a solution of methyl 3-cyclohexyl-2-(3,5-dichlorophenoxy)propanoate (0.344 g, 1.04 mmol) in THF (3 mL) was added a 1M solution of LiOH in H$_2$O (1.56 mL, 1.56 mmol) and the reaction mixture was stirred at room temperature overnight. The mixture was acidified with a 1M HCl solution (3 mL) and extracted with EtOAc (2×15 mL). Combined organics were washed with brine, dried over Na$_2$SO$_4$, filtered and evaporated to dryness to give the title compound (0.323 g, 96%) as an off-white solid. MS: 315.2 (M−H$^-$).

Intermediate B-8

(R)-2-(3,5-Dichlorophenoxy)-3-phenylpropanoic acid

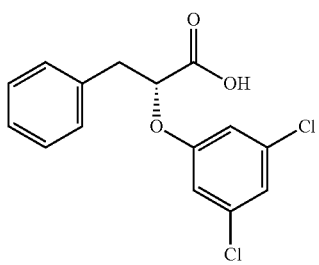 [SMILES: O=C(O)[C@@H](Cc1ccccc1)Oc1cc(Cl)cc(Cl)c1]

In analogy to the procedure described for the preparation of intermediate B-7, methyl (2S)-2-hydroxy-3-phenyl-propanoate has been reacted with 3,5-dichlorophenol, triphenylphosphine and DIAD under Mitsunobu conditions (step [A]), followed by hydrolysis with an aqueous solution of LiOH (step [B]) to give the title compound as an off white solid. MS: 309.1 (M−H$^-$).

Intermediate B-9

(R)-2-(3,5-Difluorophenoxy)-3-phenylpropanoic acid

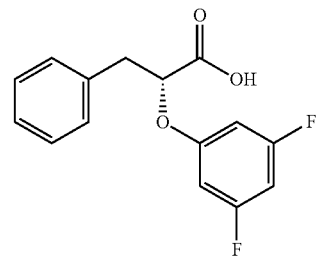 [SMILES: O=C(O)[C@@H](Cc1ccccc1)Oc1cc(F)cc(F)c1]

In analogy to the procedure described for the preparation of intermediate B-7, methyl (2S)-2-hydroxy-3-phenyl-propanoate has been reacted with 3,5-difluorophenol, triphenylphosphine and DIAD under Mitsunobu conditions (step [A]), followed by hydrolysis with an aqueous solution of LiOH (step [B]) to give the title compound as colorless oil. MS: 277.2 (M−H$^-$).

Intermediate B-10

2-(3,4-Dichlorophenoxy)-3-(3,4-dichlorophenyl)propanoic acid

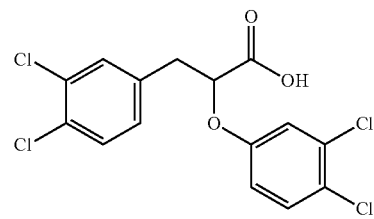 [SMILES: O=C(O)C(Cc1ccc(Cl)c(Cl)c1)Oc1ccc(Cl)c(Cl)c1]

In analogy to the procedure described for the preparation of intermediate B-7, methyl 3-(3,4-dichlorophenyl)-2-hydroxy-propanoate has been reacted with 3,4-dichlorophenol, triphenylphosphine and DIAD under Mitsunobu conditions (step [A]), followed by hydrolysis with an aqueous solution of LiOH (step [B]) to give the title compound as an orange solid.

Intermediate B-11

2-(3,5-Dichlorophenoxy)-3-(pyrazin-2-yl)propanoic acid

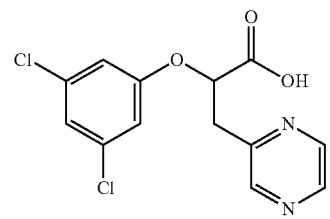 [SMILES: O=C(O)C(Cc1cnccn1)Oc1cc(Cl)cc(Cl)c1]

[A] Ethyl 3-(pyrazin-2-yl)oxirane-2-carboxylate

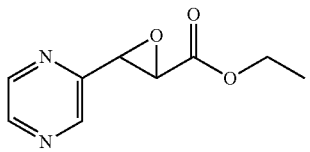

Ethyl 2-chloroacetate (0.38 g, 3.1 mmol) and pyrazine-2-carbaldehyde (0.335 g, 3.1 mmol) were dissolved in THF (5 mL) and the mixture was cooled to −78° C. A solution of NaHMDS (3.1 mL, 3.1 mmol) in THF was added dropwise. The reaction mixture was stirred at −78° C. for 30 min, then warmed up to room temperature and stirring was continued for 1 h. The dark red solution was diluted with EtOAc, poured into water (15 mL) and the aqueous layer was extracted with EtOAc (2×25 mL). Combined organics were washed with water and brine, dried over $Na_2SO_4$, filtered and evaporated to dryness to give the title compound (0.526 g, 87%) as a red oil. The crude material was used in the next step. MS: 195.0 $(M+H^+)$.

[B] Ethyl 2-hydroxy-3-(pyrazin-2-yl)propanoate

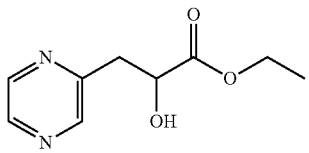

A solution of ethyl 3-(pyrazin-2-yl)oxirane-2-carboxylate (0.52 g, 2.68 mmol) in EtOAc (10 mL) was purged several times with Ar, then $Pd(OH)_2$ on carbon (0.376 g, 0.536 mmol) was added and the mixture was stirred under hydrogen atmosphere at room temperature overnight. The reaction mixture was filtered through a Whatman filter, washed with EtOAc and the resulting solution was evaporated to dryness. The residue was purified by silica gel flash chromatography, eluting with a 0 to 10% MeOH-DCM gradient to give the title compound (0.132 g, 25%) as an orange oil. MS: 197.0 $(M+H^+)$.

[C] Ethyl 2-(3,5-dichlorophenoxy)-3-(pyrazin-2-yl)propanoate

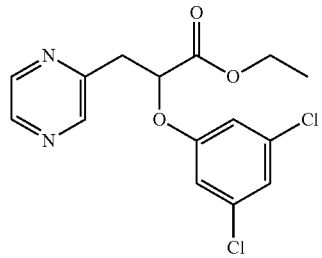 [SMILES: CCOC(=O)C(Cc1cnccn1)Oc1cc(Cl)cc(Cl)c1]

A solution of DIAD (0.163 g, 0.807 mmol) in THF (1 mL) was added dropwise to a mixture of ethyl 2-hydroxy-3-(pyrazin-2-yl)propanoate (0.132 g, 0.673 mmol), 3,5-dichlorophenol (0.121 g, 0.740 mmol) and triphenylphosphine (0.194 g, 0.74 mmol) in THF (2 mL) cooled to 0° C. with an ice bath. The mixture was then stirred at room temperature for 3 h. It was then diluted with EtOAc, poured into water (10 mL) and the aqueous layer was extracted with EtOAc (2×20 mL). Combined organics were washed with brine, dried over $Na_2SO_4$, filtered and evaporated to dryness. The residue was purified by silica gel flash chromatography, eluting with a 0 to 50% EtOAc-heptane gradient to give the title compound (0.18 g, 78%) as a colorless oil. MS: 341.0 $(M+H^+)$.

[D] 2-(3,5-Dichlorophenoxy)-3-(pyrazin-2-yl)propanoic acid

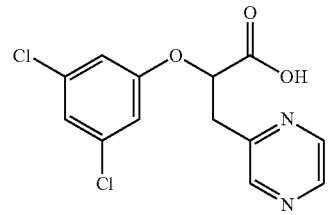 [SMILES: O=C(O)C(Cc1cnccn1)Oc1cc(Cl)cc(Cl)c1]

To a solution of ethyl 2-(3,5-dichlorophenoxy)-3-(pyrazin-2-yl)propanoate (0.232 g, 0.68 mmol) in THF (3 mL) was added a 1M solution of LiOH in $H_2O$ (1.02 mL, 1.02 mmol) and the reaction mixture was stirred at room temperature for 3 h. The mixture was acidified with a 1M HCl solution (2 mL) and extracted with EtOAc (2×15 mL). Combined organics were washed with brine, dried over $Na_2SO_4$, filtered and evaporated to dryness to give the title compound (0.202 g, 80% purity, 74%) as a light brown solid. The crude material was used in the next step. MS: 313.0 $(M+H^+)$.

Intermediate B-12

2-(3,5-Dichlorophenoxy)-3-(2-pyridyl)propanoic acid

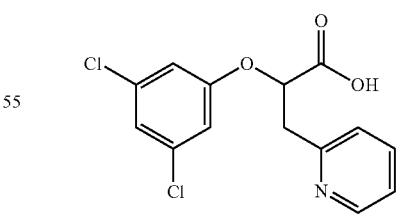

In analogy to the procedure described for the preparation of intermediate B-11 ethyl 2-chloroacetate has been reacted with pyridine-2-carbaldehyde and NaHMDS (step [A]), followed by epoxide reduction with $Pd(OH)_2$ on carbon under hydrogen atmosphere (step [B]) to give ethyl 2-hydroxy-3-(2-pyridyl)propanoate. Ethyl 2-hydroxy-3-(2-- pyridyl)propanoate has then been reacted with 3,5-dichlorophenol, triphenylphosphine and DIAD under Mitsunobu conditions (step [C]), followed by ester hydrolysis with an aqueous solution of LiOH (step [D]) to give the title compound as light brown solid. MS: 312.0 (M+H$^+$).

Intermediate B-13

Lithium 2-(3,5-dichlorophenoxy)-3-(pyridin-3-yl)propanoate

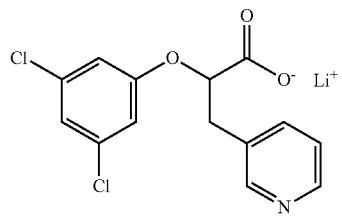 [SMILES: O=C([O-])C(Cc1cccnc1)Oc1cc(Cl)cc(Cl)c1 ; [Li+]]

In analogy to the procedure described for the preparation of intermediate B-11, ethyl 2-chloroacetate has been reacted with nicotinaldehyde and NaHMDS (step [A]), followed by epoxide reduction with Pd(OH)$_2$ on carbon under hydrogen atmosphere (step [B]) to give ethyl 2-hydroxy-3-(3-pyridyl) propanoate. Ethyl 2-hydroxy-3-(3-pyridyl)propanoate has then been reacted with 3,5-dichlorophenol, triphenylphosphine and DIAD under Mitsunobu conditions (step [C]), followed by ester hydrolysis with an aqueous solution of LiOH (step [D]) to give the lithium salt of the title compound (which precipitates in THF upon heating) as white solid. MS: 312.0 (M+H$^+$).

Example 1

(2S)-2-[3-(3,4-Dichlorophenyl)propanoylamino]-3-phenyl-N-[(3S)-1,1,1-trifluoro-4-methyl-2-oxopentan-3-yl]propanamide

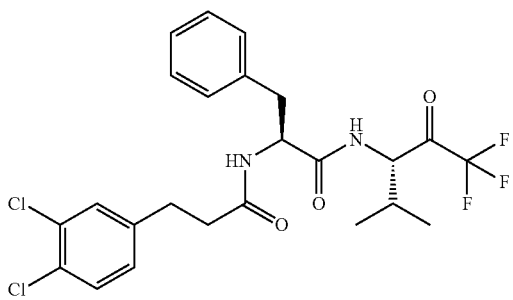 [SMILES: CC(C)[C@H](NC(=O)[C@H](Cc1ccccc1)NC(=O)CCc1ccc(Cl)c(Cl)c1)C(=O)C(F)(F)F]

To a suspension of (2S)-2-[3-(3,4-dichlorophenyl)propanoylamino]-3-phenyl-N-[(1S,2S)-3,3,3-trifluoro-2-hydroxy-1-isopropyl-propyl]propanamide (intermediate A-1) (0.058 g, 0.112 mmol) in DCM (1 mL) was added 15% Dess-Martin periodinane in DCM solution (0.348 mL, 0.168 mmol) and the reaction mixture was stirred at room temperature for 2 h. A spatula of solid Na$_2$S$_2$O$_3$ was added and stirring was continued for 5 min. The resulting white suspension was diluted with DCM/water, poured into a sat. NaHCO$_3$ solution (5 mL) and then extracted with DCM (10 mL). The organic layer was washed with brine, dried over Na$_2$SO$_4$, filtered and evaporated. The residue was purified by silica gel flash chromatography, eluting with a 0-50% EtOAc-heptane gradient to give the title compound (0.025 g, 43%) as a colorless solid. MS: 517.2 (M+H$^+$).

The following examples listed in Table 1 were prepared in analogy to the procedures described for the preparation of example 1 and intermediate A-1 by using the indicated starting materials (phenylglycine synthons can undergo isomerization at variable extent during coupling, thus the stereochemistry of the final compounds is described as S and R unless the S and the R isomers have been separated by HPLC chromatography):

TABLE 1

| Ex | Name Aspect | Reactant | MS (M + H$^+$) |
|---|---|---|---|
| 2 | (2S)-2-[[2-(3-Chlorophenoxy)acetyl]amino]-3-phenyl-N-[(3S)-1,1,1-trifluoro-4-methyl-2-oxopentan-3-yl]propanamide 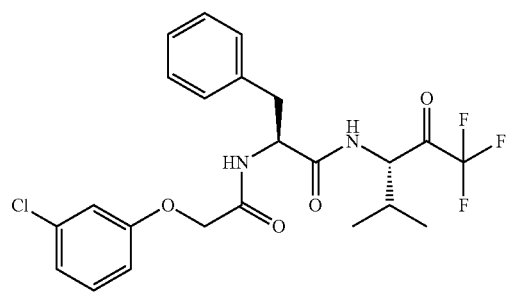 colorless solid | 2-(3-chlorophenoxy)acetic acid (to be used in step [C]) | 485.2 |

TABLE 1-continued

| Ex | Name Aspect | Reactant | MS (M + H+) |
|---|---|---|---|
| 3 | (2S)-2-[[2-(3,4-Dichlorophenoxy)acetyl]amino]-3-phenyl-N-[(3S)-1,1,1-trifluoro-4-methyl-2-oxopentan-3-yl]propanamide 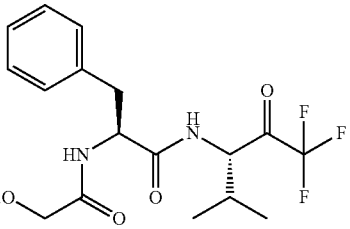 colorless amorphous solid | 2-(3,4-dichlorophenoxy)acetic acid (to be used in step [C]) | 519.1 |
| 4 | (2S)-2-[[(3R/S)-(3-Chlorophenyl)-3-phenylpropanoyl]amino]-3-phenyl-N-[(3S)-1,1,1-trifluoro-4-methyl-2-oxopentan-3-yl]propanamide 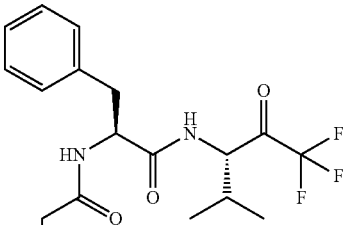 colorless solid | 3-(3-chlorophenyl)-3-phenyl-propanoic acid (to be used in step [C]) | 559.2 |
| 5 | (2S)-2-(3,3-Diphenylpropanoylamino)-3-phenyl-N-[(3S)-1,1,1-trifluoro-4-methyl-2-oxopentan-3-yl]propanamide 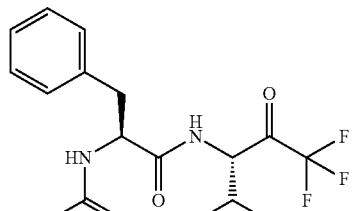 colorless amorphous solid | 3,3-diphenylpropanoic acid (to be used in step [C]) | 525.4 |

TABLE 1-continued

| Ex | Name / Aspect | Reactant | MS (M + H⁺) |
|----|---------------|----------|-------------|
| 6 | (2S)-2-[[(3R/S)-(4-Chlorophenyl)-3-(4-methoxyphenoxy)propanoyl]amino]-3-phenyl-N-[(3S)-1,1,1-trifluoro-4-methyl-2-oxopentan-3-yl]propanamide<br><br>colorless amorphous solid | 3-(4-chlorophenyl)-3-(4-methoxyphenoxy)propanoic acid (intermediate B-2) (to be used in step [C]) | (M − H⁻) 603.2 |
| 7 | (2S)-3-(4-Chlorophenyl)-2-[[(3R/S)-(4-chlorophenyl)-3-(4-methoxyphenoxy)propanoyl]amino]-N-[(3S)-1,1,1-trifluoro-4-methyl-2-oxopentan-3-yl]propanamide<br><br>colorless amorphous solid | (2S)-2-(tert-butoxycarbonylamino)-3-(4-chlorophenyl)propanoic acid (to be used in step [A])<br>3-(4-chlorophenyl)-3-(4-methoxyphenoxy)propanoic acid (intermediate B-2) (to be used in step [C]) | 639.3 |
| 8 | (2S)-2-[[(E)-3-(4-Chlorophenyl)prop-2-enoyl]amino]-3-phenyl-N-[(3S)-1,1,1-trifluoro-4-methyl-2-oxopentan-3-yl]propanamide<br><br>colorless amorphous solid | (E)-3-(4-chlorophenyl)prop-2-enoic acid (to be used in step [C]) | 481.3 |

TABLE 1-continued

| Ex | Name Aspect | Reactant | MS (M + H⁺) |
|---|---|---|---|
| 9 | (2S)-3-(4-Chlorophenyl)-2-[[(3R/S)-(4-chlorophenyl)-3-(4-methoxyphenyl)propanoyl]amino]-N-[(3S)-1,1,1-trifluoro-4-methyl-2-oxopentan-3-yl]propanamide<br><br>off-white solid | (2S)-2-(tert-butoxycarbonylamino)-3-(4-chlorophenyl)propanoic acid (to be used in step [A]) 3-(4-chlorophenyl)-3-(4-methoxyphenyl) propanoic acid (intermediate B-5 to be used in step [C]) | 623.2 |
| 10 | (2S)-3-(4-Chlorophenyl)-2-[[(3R/S)-(4-chlorophenyl)-3-phenylpropanoyl]amino]-N-[(3S)-1,1,1-trifluoro-4-methyl-2-oxopentan-3-yl]propanamide<br><br>colorless solid | (2S)-2-(tert-butoxycarbonylamino)-3-(4-chlorophenyl)propanoic acid (to be used in step [A]) 3-(4-chlorophenyl)-3-phenyl-propanoic acid (to be used in step [C]) | 593.3 |
| 11 | (2S)-3-(4-Chlorophenyl)-2-[[(3R/S)-(3-chlorophenyl)-3-(4-methoxyphenoxy)propanoyl]amino]-N-[(3S)-1,1,1-trifluoro-4-methyl-2-oxopentan-3-yl]propanamide<br><br>off-white solid | (2S)-2-(tert-butoxycarbonylamino)-3-(4-chlorophenyl)propanoic acid (to be used in step [A]) 3-(3-chlorophenyl)-3-(4-methoxyphenoxy) propanoic acid (intermediate B-1) (to be used in step [C]) | 639.2 |

TABLE 1-continued

| Ex | Name<br>Aspect | Reactant | MS<br>(M + H⁺) |
|---|---|---|---|
| 12 | (2S)-3-(4-Chlorophenyl)-2-[[(3R/S)-(3,4-dichlorophenyl)-3-(4-methoxyphenyl)propanoyl]amino]-N-[(3S)-1,1,1-trifluoro-4-methyl-2-oxopentan-3-yl]propanamide<br><br>colorless solid | (2S)-2-(tert-butoxycarbonylamino)-3-(4-chlorophenyl)propanoic acid (to be used in step [A])<br>3-(3,4-dichlorophenyl)-3-(4-methoxyphenyl) propanoic acid (intermediate B-6 to be used in step [C]) | 657.3 |
| 13 | (2S)-2-[[(3R/S)-(4-Chlorophenyl)-3-(4-methoxyphenyl)propanoyl]amino]-3-pyridin-2-yl-N-[(3S)-1,1,1-trifluoro-4-methyl-2-oxopentan-3-yl]propanamide<br><br>colorless solid | (2S)-2-(tert-butoxycarbonylamino)-3-(2-pyridyl)propanoic acid (to be used in step [A])<br>3-(4-chlorophenyl)-3-(4-methoxyphenyl) propanoic acid (intermediate B-5 to be used in step [C]) | 590.4 |
| 14 | (2S)-3-(4-Chlorophenyl)-2-[[(E)-3-(3,4-dichlorophenyl)prop-2-enoyl]amino]-N-[(3S)-1,1,1-trifluoro-4-methyl-2-oxopentan-3-yl]propanamide<br><br>colorless solid | (2S)-2-(tert-butoxycarbonylamino)-3-(4-chlorophenyl)propanoic acid (to be used in step [A])<br>(E)-3-(3,4-dichlorophenyl)prop-2-enoic acid (to be used in step [C]) | 551.2 |

TABLE 1-continued

| Ex | Name / Aspect | Reactant | MS (M + H⁺) |
|---|---|---|---|
| 15 | (2S)-3-(3-Chlorophenyl)-2-[3-(3,4-dichlorophenyl)propanoylamino]-N-[(3S)-1,1,1-trifluoro-4-methyl-2-oxopentan-3-yl]propanamide<br><br>colorless solid | (2S)-2-(tert-butoxycarbonylamino)-3-(3-chlorophenyl)propanoic acid (to be used in step [A])<br>3-(3,4-dichlorophenyl)propanoic acid (to be used in step [C]) | 553.3 |
| 16 | (2S)-3-(3-Chlorophenyl)-2-[[(3R/S)-(3,4-dichlorophenyl)-3-(4-methoxyphenyl)propanoyl]amino]-N-[(3S)-1,1,1-trifluoro-4-methyl-2-oxopentan-3-yl]propanamide<br><br>off-white solid | (2S)-2-(tert-butoxycarbonylamino)-3-(3-chlorophenyl)propanoic acid (to be used in step [A])<br>3-(3,4-dichlorophenyl)-3-(4-methoxyphenyl) propanoic acid (intermediate B-6 to be used in step [C]) | 659.3 |
| 17 | (2S)-3-(3-Chlorophenyl)-2-[[(3R/S)-(4-chlorophenyl)-3-(4-methoxyphenyl)propanoyl]amino]-N-[(3S)-1,1,1-trifluoro-4-methyl-2-oxopentan-3-yl]propanamide<br><br>colorless amorphous solid | (2S)-2-(tert-butoxycarbonylamino)-3-(3-chlorophenyl)propanoic acid (to be used in step [A])<br>3-(4-chlorophenyl)-3-(4-methoxyphenyl) propanoic acid (intermediate B-5 to be used in step [C]) | 623.3 |

TABLE 1-continued

| Ex | Name Aspect | Reactant | MS (M + H+) |
|---|---|---|---|
| 18 | (2S)-3-(3-Chlorophenyl)-2-[[(3R/S)-(4-chlorophenyl)-3-(4-methoxyphenoxy)propanoyl]amino]-N-[(3S)-1,1,1-trifluoro-4-methyl-2-oxopentan-3-yl]propanamide<br><br>colorless amorphous solid | (2S)-2-(tert-butoxycarbonylamino)-3-(3-chlorophenyl)propanoic acid (to be used in step [A])<br>3-(4-chlorophenyl)-3-(4-methoxyphenoxy)propanoic acid (intermediate B-2) (to be used in step [C]) | 639.4 |
| 19 | (2S)-3-(3-Chlorophenyl)-2-[[(E)-3-(3,4-dichlorophenyl)prop-2-enoyl]amino]-N-[(3S)-1,1,1-trifluoro-4-methyl-2-oxopentan-3-yl]propanamide<br><br>colorless solid | (2S)-2-(tert-butoxycarbonylamino)-3-(3-chlorophenyl)propanoic acid (to be used in step [A])<br>(E)-3-(3,4-dichlorophenyl)prop-2-enoic acid (to be used in step [C]) | 549.2 |
| 20 | (2S)-3-(3-Chlorophenyl)-2-[3-(3,5-dichlorophenyl)propanoylamino]-N-[(3S)-1,1,1-trifluoro-4-methyl-2-oxopentan-3-yl]propanamide<br><br>colorless amorphous solid | (2S)-2-(tert-butoxycarbonylamino)-3-(3-chlorophenyl)propanoic acid (to be used in step [A])<br>3-(3,5-dichlorophenyl)propanoic acid (to be used in step [C]) | 551.1 |

TABLE 1-continued

| Ex | Name Aspect | Reactant | MS (M + H+) |
|---|---|---|---|
| 21 | (2S)-3-(4-Chlorophenyl)-2-[[2-(3,5-dichlorophenoxy)acetyl]amino]-N-[(3S)-1,1,1-trifluoro-4-methyl-2-oxopentan-3-yl]propanamide<br><br>colorless solid | (2S)-2-(tert-butoxycarbonylamino)-3-(4-chlorophenyl)propanoic acid (to be used in step [A])<br>2-(3,5-dichlorophenoxy)acetic acid (to be used in step [C]) | 555.2 |
| 22 | (2S)-3-(4-Chlorophenyl)-2-[[(E)-3-(3,5-dichlorophenyl)prop-2-enoyl]amino]-N-[(3S)-1,1,1-trifluoro-4-methyl-2-oxopentan-3-yl]propanamide<br><br>colorless solid | (2S)-2-(tert-butoxycarbonylamino)-3-(4-chlorophenyl)propanoic acid (to be used in step [A])<br>((E)-3-(3,5-dichlorophenyl)prop-2-enoic acid (to be used in step [C]) | 551.2 |
| 23 | 3-(3,4-Dichlorophenyl)-N-[(1S and 1R)-2-oxo-1-phenyl-2-[[(3S)-1,1,1-trifluoro-4-methyl-2-oxopentan-3-yl]amino]ethyl]propanamide<br><br>colorless solid | (2S)-2-(tert-butoxycarbonylamino)-2-phenyl-acetic acid (to be used in step [A])<br>3-(3,4-dichlorophenyl)propanoic acid (to be used in step [C]) | 503.2 |

TABLE 1-continued

| Ex | Name Aspect | Reactant | MS (M + H⁺) |
|---|---|---|---|
| 24 | (3R/S)-(3-Chlorophenyl)-N-[(1S and 1R)-2-oxo-1-phenyl-2-[[(3S)-1,1,1-trifluoro-4-methyl-2-oxopentan-3-yl]amino]ethyl]-3-phenylpropanamide<br><br>colorless solid | (2S)-2-(tert-butoxycarbonylamino)-2-phenyl-acetic acid (to be used in step [A])<br>3-(3-chlorophenyl)-3-phenyl-propanoic acid (to be used in step [C]) | 563.3 (+H₂O) |
| 25 | (2S)-2-[[2-(3-Chlorophenoxy)acetyl]-methylamino]-3-phenyl-N-[(3S)-1,1,1-trifluoro-4-methyl-2-oxopentan-3-yl]propanamide<br><br>colorless amorphous solid | (2S)-2-[tert-butoxycarbonyl(methyl)amino]-3-phenyl-propanoic acid (to be used in step [A])<br>2-(3-chlorophenoxy)acetic acid (to be used in step [C]) | 499.3 |
| 26 | (2S)-2-[[(3R/S)-(3-Chlorophenyl)-3-phenylpropanoyl]-methylamino]-3-phenyl-N-[(3S)-1,1,1-trifluoro-4-methyl-2-oxopentan-3-yl]propanamide<br><br>colorless amorphous solid | (2S)-2-[tert-butoxycarbonyl(methyl)amino]-3-phenyl-propanoic acid (to be used in step [A])<br>3-(3-chlorophenyl)-3-phenyl-propanoic acid (to be used in step [C]) | 575.2 |

TABLE 1-continued

| Ex | Name / Aspect | Reactant | MS (M + H⁺) |
|---|---|---|---|
| 27 | 5-Chloro-N-[(2S)-3-(3-chlorophenyl)-1-oxo-1-[[(3S)-1,1,1-trifluoro-4-methyl-2-oxopentan-3-yl]amino]propan-2-yl]-1-benzothiophene-3-carboxamide<br><br>colorless solid | (2S)-2-(tert-butoxycarbonylamino)-3-(3-chlorophenyl)propanoic acid (to be used in step [A])<br>5-chlorobenzothiophene-3-carboxylic acid (to be used in step [C]) | 547.2 |
| 28 | (E)-3-(3,4-Dichlorophenyl)-N-[(1S and 1R)-2-oxo-1-phenyl-2-[[(3S)-1,1,1-trifluoro-4-methyl-2-oxopentan-3-yl]amino]ethyl]prop-2-enamide<br><br>colorless amorphous solid | (2S)-2-(tert-butoxycarbonylamino)-2-phenyl-acetic acid (to be used in step [A])<br>((E)-3-(3,4-dichlorophenyl)prop-2-enoic acid (to be used in step [C]) | 501.2 |
| 29 | (2S and 2R)-2-[[2-(3,5-Dichlorophenoxy)acetyl]amino]-2-phenyl-N-[(3S)-1,1,1-trifluoro-4-methyl-2-oxopentan-3-yl]acetamide<br><br>colorless amorphous solid | (2S)-2-(tert-butoxycarbonylamino)-2-phenyl-acetic acid (to be used in step [A])<br>2-(3,5-dichlorophenoxy)acetic acid (to be used in step [C]) | 505.2 |

TABLE 1-continued

| Ex | Name Aspect | Reactant | MS (M + H⁺) |
|---|---|---|---|
| 30 | N-[(1S and 1R)-1-(4-Chlorophenyl)-2-oxo-2-[[(3S)-1,1,1-trifluoro-4-methyl-2-oxopentan-3-yl]amino]ethyl]-3-(3,4-dichlorophenyl)propanamide<br><br>colorless amorphous solid | (2S)-2-(tert-butoxycarbonylamino)-2-(4-chlorophenyl)acetic acid (to be used in step [A])<br>3-(3,4-dichlorophenyl)propanoic acid (to be used in step [C]) | 537.1 |
| 31 | (3R/S)-(3-Chlorophenyl)-N-[(1S and 1R)-1-(4-chlorophenyl)-2-oxo-2-[[(3S)-1,1,1-trifluoro-4-methyl-2-oxopentan-3-yl]amino]ethyl]-3-phenylpropanamide<br><br>colorless amorphous solid | (2S)-2-(tert-butoxycarbonylamino)-2-(4-chlorophenyl)acetic acid (to be used in step [A])<br>3-(3-chlorophenyl)-3-phenyl-propanoic acid (to be used in step [C]) | 597.1 (+H₂O) |
| 32 | (2S)-3-(3-Chlorophenyl)-2-[[(3R/S)-(3,4-dichlorophenyl)-3-(4-methoxyphenoxy)propanoyl]amino]-N-[(3S)-1,1,1-trifluoro-4-methyl-2-oxopentan-3-yl]propanamide<br><br>colorless solid | (2S)-2-(tert-butoxycarbonylamino)-3-(3-chlorophenyl)propanoic acid (to be used in step [A])<br>3-(3,4-dichlorophenyl)-3-(4-methoxyphenoxy) propanoic acid (intermediate B-3) (to be used in step [C]) | 673.2 |

TABLE 1-continued

| Ex | Name Aspect | Reactant | MS (M + H+) |
|---|---|---|---|
| 33 | (E)-N-[(1S and 1R)-1-(4-Chlorophenyl)-2-oxo-2-[[(3S)-1,1,1-trifluoro-4-methyl-2-oxopentan-3-yl]amino]ethyl]-3-(3,4-dichlorophenyl)prop-2-enamide<br><br>colorless solid | (2S)-2-(tert-butoxycarbonylamino)-2-(4-chlorophenyl)acetic acid (to be used in step [A])<br>(E)-3-(3,4-dichlorophenyl)prop-2-enoic acid (to be used in step [C]) | 535.1 |
| 34 | 3-(4-Chlorophenyl)-N-[(2S)-3-(3-chlorophenyl)-1-oxo-1-[[(3S)-1,1,1-trifluoro-4-methyl-2-oxopentan-3-yl]amino]propan-2-yl]-(2R/S)-(4-methoxyphenyl)propanamide<br><br>colorless solid | (2S)-2-(tert-butoxycarbonylamino)-3-(3-chlorophenyl)propanoic acid (to be used in step [A])<br>3-(4-Chlorophenyl)-2-(4-methoxyphenyl) propanoic acid (intermediate B-4 to be used in step [C]) | 623.2 |
| 35 | (2S and 2R)-2-(4-Chlorophenyl)-2-[[2-(3,5-dichlorophenoxy)acetyl]amino]-N-[(3S)-1,1,1-trifluoro-4-methyl-2-oxopentan-3-yl]acetamide<br><br>colorless solid | (2S)-2-(tert-butoxycarbonylamino)-2-(4-chlorophenyl)acetic acid (to be used in step [A])<br>2-(3,5-dichlorophenoxy)acetic acid (to be used in step [C]) | 557.1 (+H$_2$O) |

TABLE 1-continued

| Ex | Name / Aspect | Reactant | MS (M + H+) |
|---|---|---|---|
| 36 | (2S and 2R)-2-[[(2R/S)-(3,5-Dichlorophenoxy)-2-phenylacetyl]amino]-2-phenyl-N-[(3S)-1,1,1-trifluoro-4-methyl-2-oxopentan-3-yl]acetamide<br><br>colorless solid | (2S)-2-(tert-butoxycarbonylamino)-2-phenyl-acetic acid (to be used in step [A])<br>2-(3,5-dichlorophenoxy)-2-phenyl-acetic acid (to be used in step [C]) | 581.2 |
| 37 | 6-Chloro-N-[(1S and 1R)-2-oxo-1-phenyl-2-[[(3S)-1,1,1-trifluoro-4-methyl-2-oxopentan-3-yl]amino]ethyl]-3-phenyl-1-benzofuran-2-carboxamide<br><br>colorless solid | (2S)-2-(tert-butoxycarbonylamino)-2-phenyl-acetic acid (to be used in step [A])<br>6-chloro-3-phenyl-benzofuran-2-carboxylic acid (to be used in step [C]) | 575.1 (+H$_2$O) |
| 38 | 7-Bromo-5-chloro-N-[(1S and 1R)-2-oxo-1-phenyl-2-[[(3S)-1,1,1-trifluoro-4-methyl-2-oxopentan-3-yl]amino]ethyl]-1-benzofuran-2-carboxamide<br><br>colorless solid | (2S)-2-(tert-butoxycarbonylamino)-2-phenyl-acetic acid (to be used in step [A])<br>7-bromo-5-chloro-benzofuran-2-carboxylic acid (to be used in step [C]) | 577.0 (+H$_2$O) |

TABLE 1-continued

| Ex | Name / Aspect | Reactant | MS (M + H⁺) |
|---|---|---|---|
| 39 | 3-Cyclohexyl-N-[(1S and 1R)2-oxo-1-phenyl-2-[[(3S)-1,1,1-trifluoro-4-methyl-2-oxopentan-3-yl]amino]ethyl]propanamide<br><br>colorless amorphous solid | (2S)-2-(tert-butoxycarbonylamino)-2-phenyl-acetic acid (to be used in step [A])<br>3-cyclohexylpropanoic acid (to be used in step [C]) | 459.3 (+H$_2$O) |
| 40 | 5,7-Dichloro-N-[(1S and 1R)-2-oxo-1-phenyl-2-[[(3S)-1,1,1-trifluoro-4-methyl-2-oxopentan-3-yl]amino]ethyl]-3-phenyl-1-benzofuran-2-carboxamide<br><br>colorless amorphous solid | (2S)-2-(tert-butoxycarbonylamino)-2-phenyl-acetic acid (to be used in step [A])<br>5,7-dichloro-3-phenyl-benzofuran-2-carboxylic acid (to be used in step [C]) | 591.1 |
| 41 | (2S and 2R)-2-[[2-(2-Adamantyl)acetyl]amino]-2-phenyl-N-[(3S)-1,1,1-trifluoro-4-methyl-2-oxopentan-3-yl]acetamide<br><br>colorless amorphous solid | (2S)-2-(tert-butoxycarbonylamino)-2-phenyl-acetic acid (to be used in step [A])<br>2-(2-adamantyl)acetic acid (to be used in step [C]) | 497.3 (+H$_2$O) |

TABLE 1-continued

| Ex | Name / Aspect | Reactant | MS (M + H⁺) |
|---|---|---|---|
| 42 | (2S,3S)-2-[3-(3,4-Dichlorophenyl)propanoylamino]-3-phenyl-N-[(3S)-1,1,1-trifluoro-4-methyl-2-oxopentan-3-yl]butanamide<br><br>colorless solid | (2S,3S)-2-((tert-butoxycarbonyl)amino)-3-phenylbutanoic acid (to be used in step [A])<br>3-(3,4-dichlorophenyl)propanoic acid (to be used in step [C]) | 531.1 |
| 43 | (2S,3S)-2-[[(3R/S)-(3-Chlorophenyl)-3-phenylpropanoyl]amino]-3-phenyl-N-[(3S)-1,1,1-trifluoro-4-methyl-2-oxopentan-3-yl]butanamide<br><br>colorless solid | (2S,3S)-2-((tert-butoxycarbonyl)amino)-3-phenylbutanoic acid (to be used in step [A])<br>3-(3-chlorophenyl)-3-phenyl-propanoic acid (to be used in step [C]) | 573.2 |
| 44 | (2S)-2-[3-(3,4-Dichlorophenyl)propanoylamino]-4-phenyl-N-[(3S)-1,1,1-trifluoro-4-methyl-2-oxopentan-3-yl]butanamide<br><br>colorless solid | (2S)-2-(tert-butoxycarbonylamino)-4-phenyl-butanoic acid (to be used in step [A])<br>3-(3,4-dichlorophenyl)propanoic acid (to be used in step [C]) | 531.2 |

TABLE 1-continued

| Ex | Name / Aspect | Reactant | MS (M + H⁺) |
|---|---|---|---|
| 45 | (2S)-2-[[(3R/S)-(3-Chlorophenyl)-3-phenylpropanoyl]amino]-4-phenyl-N-[(3S)-1,1,1-trifluoro-4-methyl-2-oxopentan-3-yl]butanamide<br><br>colorless solid | (2S)-2-(tert-butoxycarbonylamino)-4-phenyl-butanoic acid (to be used in step [A])<br>3-(3-chlorophenyl)-3-phenyl-propanoic acid (to be used in step [C]) | 573.3 |
| 46 | 3-(3,4-Dichlorophenyl)-N-[(1S or 1R)-1-(3-methoxyphenyl)-2-oxo-2-[[(3S)-1,1,1-trifluoro-4-methyl-2-oxopentan-3-yl]amino]ethyl]propanamide<br><br>colorless solid | (2S)-2-(tert-butoxycarbonylamino)-2-(3-methoxyphenyl)acetic acid (to be used in step [A])<br>3-(3,4-dichlorophenyl)propanoic acid (to be used in step [C])<br>Purified by HPLC chromatography | 533.3 |
| 47 | 3-(3,4-Dichlorophenyl)-N-[(1R or 1S)-1-(3-methoxyphenyl)-2-oxo-2-[[(3S)-1,1,1-trifluoro-4-methyl-2-oxopentan-3-yl]amino]ethyl]propanamide<br><br>colorless solid | (2S)-2-(tert-butoxycarbonylamino)-2-(3-methoxyphenyl)acetic acid (to be used in step [A])<br>3-(3,4-dichlorophenyl)propanoic acid (to be used in step [C])<br>Purified by HPLC chromatography | 533.1 |

TABLE 1-continued

| Ex | Name / Aspect | Reactant | MS (M + H+) |
|---|---|---|---|
| 48 | (2S or 2R)-2-[[2-(3,5-Dichlorophenoxy)acetyl]amino]-2-(3-methoxyphenyl)-N-[(3S)-1,1,1-trifluoro-4-methyl-2-oxopentan-3-yl]acetamide<br>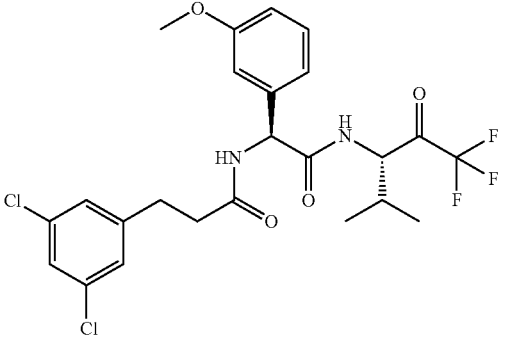<br>off-white amorphous solid | (2S)-2-(tert-butoxycarbonylamino)-2-(3-methoxyphenyl)acetic acid (to be used in step [A])<br>2-(3,5-dichlorophenoxy)acetic acid (to be used in step [C])<br>Purified by HPLC chromatography | 535.1 |
| 49 | (2R or 2S)-2-[[2-(3,5-Dichlorophenoxy)acetyl]amino]-2-(3-methoxyphenyl)-N-[(3S)-1,1,1-trifluoro-4-methyl-2-oxopentan-3-yl]acetamide<br>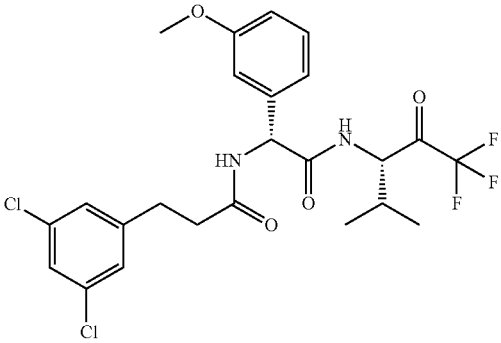<br>off-white amorphous solid | (2S)-2-(tert-butoxycarbonylamino)-2-(3-methoxyphenyl)acetic acid (to be used in step [A])<br>2-(3,5-dichlorophenoxy)acetic acid (to be used in step [C])<br>Purified by HPLC chromatography | 535.1 |
| 50 | (E)-3-(3,4-Dichlorophenyl)-N-[(1S or 1R)-1-(3-methoxyphenyl)-2-oxo-2-[[(3S)-1,1,1-trifluoro-4-methyl-2-oxopentan-3-yl]amino]ethyl]prop-2-enamide<br>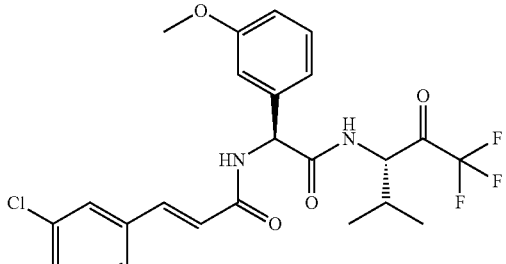<br>off-white amorphous solid | (2S)-2-(tert-butoxycarbonylamino)-2-(3-methoxyphenyl)acetic acid (to be used in step [A])<br>((E)-3-(3,4-dichlorophenyl)prop-2-enoic acid (to be used in step [C])<br>Purified by HPLC chromatography | 531.2 |

TABLE 1-continued

| Ex | Name Aspect | Reactant | MS (M + H⁺) |
|---|---|---|---|
| 51 | (E)-3-(3,4-Dichlorophenyl)-N-[(1R or 1S)-1-(3-methoxyphenyl)-2-oxo-2-[[(3S)-1,1,1-trifluoro-4-methyl-2-oxopentan-3-yl]amino]ethyl]prop-2-enamide<br><br>off-white amorphous solid | (2S)-2-(tert-butoxycarbonylamino)-2-(3-methoxyphenyl)acetic acid (to be used in step [A])<br>((E)-3-(3,4-dichlorophenyl)prop-2-enoic acid (to be used in step [C])<br>Purified by HPLC chromatography | 531.2 |
| 52 | (3R/S)-(3-Chlorophenyl)-N-[(1S or 1R)-1-(3-methoxyphenyl)-2-oxo-2-[[(3S)-1,1,1-trifluoro-4-methyl-2-oxopentan-3-yl]amino]ethyl]-3-phenylpropanamide<br><br>off-white amorphous solid | (2S)-2-(tert-butoxycarbonylamino)-2-(3-methoxyphenyl)acetic acid (to be used in step [A])<br>3-(3-chlorophenyl)-3-phenyl-propanoic acid (to be used in step [C])<br>Purified by HPLC chromatography | 575.2 |
| 53 | (3R/S)-(3-Chlorophenyl)-N-[(1R or 1S)-1-(3-methoxyphenyl)-2-oxo-2-[[(3S)-1,1,1-trifluoro-4-methyl-2-oxopentan-3-yl]amino]ethyl]-3-phenylpropanamide<br><br>off-white amorphous solid | (2S)-2-(tert-butoxycarbonylamino)-2-(3-methoxyphenyl)acetic acid (to be used in step [A])<br>3-(3-chlorophenyl)-3-phenyl-propanoic acid (to be used in step [C])<br>Purified by HPLC chromatography | 575.2 |

The following examples listed in Table 2 were prepared in analogy to the procedures described for the preparation of example 1 and intermediate A-1 by using the indicated starting materials (phenylglycine synthons can undergo isomerization at variable extent during coupling, thus the stereochemistry of the final compounds is described as S and R unless the S and the R isomers have been separated by HPLC chromatography):

TABLE 2

| Ex | Name<br>Aspect | Reactant | MS<br>(M + H+) |
|---|---|---|---|
| 54 | (2R)-2-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-phenylpropanamide<br><br>colorless solid | (2S)-2-(tert-butoxycarbonylamino)-2-phenyl-acetic acid (to be used in step [A])<br>(R)-2-(3,5-dichlorophenoxy)-3-phenylpropanoic acid (intermediate B-8 to be used in step [C]) | 595.2 |
| 55 | (2R/S)-(3,4-Dichlorophenoxy)-3-(3,4-dichlorophenyl)-N-[(1S and 1R)-2-oxo-1-phenyl-2-[[(3S)-1,1,1-trifluoro-4-methyl-2-oxopentan-3-yl]amino]ethyl]propanamide<br><br>colorless solid | (2S)-2-(tert-butoxycarbonylamino)-2-phenyl-acetic acid (to be used in step [A])<br>2-(3,4-dichlorophenoxy)-3-(3,4-dichlorophenyl)propanoic acid (intermediate B-10 to be used in step [C]) | 663.2 |
| 56 | (3R or 3S)-(4-Chlorophenyl)-2-(4-methoxyphenyl)-N-[(1S and 1R)-2-oxo-1-phenyl-2-[[(3S)-1,1,1-trifluoro-4-methyl-2-oxopentan-3-yl]amino]ethyl]propanamide<br><br>colorless waxy solid | (2S)-2-(tert-butoxycarbonylamino)-2-phenyl-acetic acid (to be used in step [A])<br>3-(4-chlorophenyl)-2-(4-methoxyphenyl)propanoic acid (intermediate B-4 to be used in step [C])<br>Purified by HPLC chromatography | 575.2 |

TABLE 2-continued

| Ex | Name Aspect | Reactant | MS (M + H+) |
|---|---|---|---|
| 57 | (3S or 3R)-(4-Chlorophenyl)-2-(4-methoxyphenyl)-N-[(1S and 1R)-2-oxo-1-phenyl-2-[[(3S)-1,1,1-trifluoro-4-methyl-2-oxopentan-3-yl]amino]ethyl]propanamide<br><br>colorless waxy solid | (2S)-2-(tert-butoxycarbonylamino)-2-phenyl-acetic acid (to be used in step [A])<br>3-(4-chlorophenyl)-2-(4-methoxyphenyl) propanoic acid (intermediate B-4 to be used in step [C])<br>Purified by HPLC chromatography | 575.2 |
| 58 | (3S or 3R)-(3,4-Dichlorophenyl)-3-(1,1-dioxo-1,4-thiazinan-4-yl)-N-[(1S and 1R)-2-oxo-1-phenyl-2-[[(3S)-1,1,1-trifluoro-4-methyl-2-oxopentan-3-yl]amino]ethyl]propanamide<br><br>colorless waxy solid | (2S)-2-(tert-butoxycarbonylamino)-2-phenyl-acetic acid (to be used in step [A])<br>3-(3,4-dichlorophenyl)-3-(1,1-dioxo-1,4-thiazinan-4-yl)propanoic acid (to be used in step [C])<br>Purified by HPLC chromatography | 636.2 |
| 59 | (3R or 3S)-(3,4-Dichlorophenyl)-3-(1,1-dioxo-1,4-thiazinan-4-yl)-N-[(1S and 1R)-2-oxo-1-phenyl-2-[[(3S)-1,1,1-trifluoro-4-methyl-2-oxopentan-3-yl]amino]ethyl]propanamide<br><br>colorless waxy solid | (2S)-2-(tert-butoxycarbonylamino)-2-phenyl-acetic acid (to be used in step [A])<br>3-(3,4-dichlorophenyl)-3-(1,1-dioxo-1,4-thiazinan-4-yl)propanoic acid (to be used in step [C])<br>Purified by HPLC chromatography | 636.2 |

TABLE 2-continued

| Ex | Name / Aspect | Reactant | MS (M + H⁺) |
|---|---|---|---|
| 60 | (S)-2-(3-(3,5-Difluorophenyl)propanamido)-3-phenyl-N-((S)-1,1,1-trifluoro-4-methyl-2-oxopentan-3-yl)propanamide<br><br>white solid | 3-(3,5-difluorophenyl)propanoic acid (to be used in step [C]) | 485.3 |
| 61 | (R)-2-(3,5-Dichlorophenoxy)-N-((S)-1-oxo-3-phenyl-1-(((S)-1,1,1-trifluoro-4-methyl-2-oxopentan-3-yl)amino)propan-2-yl)-3-phenylpropanamide<br><br>white solid | (R)-2-(3,5-Dichlorophenoxy)-3-phenylpropanoic acid (intermediate B-8 to be used in step [C]) | 609.2 |
| 62 | 3-(3,5-Difluorophenyl)-N-[(1S and 1R)-2-oxo-1-phenyl-2-[[(3S)-1,1,1-trifluoro-4-methyl-2-oxopentan-3-yl]amino]ethyl]propanamide<br><br>colorless amorphous solid | (2S)-2-(tert-butoxycarbonylamino)-2-phenyl-acetic acid (to be used in step [A])<br>3-(3,5-difluorophenyl)propanoic acid (to be used in step [C]) | (M + H2O)+ 489.2 |

TABLE 2-continued

| Ex | Name<br>Aspect | Reactant | MS<br>(M + H⁺) |
|---|---|---|---|
| 63 | (R)-2-(3,5-Difluorophenoxy)-N-((1S and 1R)-2-oxo-1-phenyl-2-(((S)-1,1,1-trifluoro-4-methyl-2-oxopentan-3-yl)amino)ethyl)-3-phenylpropanamide<br><br>off-white foam | (2S)-2-(tert-butoxycarbonylamino)-2-phenyl-acetic acid (to be used in step [A])<br>(R)-2-(3,5-difluorophenoxy)-3-phenylpropanoic acid (intermediate B-9 to be used in step [C]) | 563.2 |
| 64 | (3R/S)-Cyclohexyl-2-(3,5-dichlorophenoxy)-N-[(1S and 1R)-2-oxo-1-phenyl-2-[[(3S)-1,1,1-trifluoro-4-methyl-2-oxopentan-3-yl]amino]ethyl]propanamide<br><br>off-white solid | (2S)-2-(tert-butoxycarbonylamino)-2-phenyl-acetic acid (to be used in step [A])<br>3-cyclohexyl-2-(3,5-dichlorophenoxy)propanoic acid (intermediate B-7 to be used in step [C]) | 601.2 |
| 65 | (2S and 2R)-2-[[2-(3,5-Difluorophenoxy)acetyl]amino]-2-phenyl-N-[(3S)-1,1,1-trifluoro-4-methyl-2-oxopentan-3-yl]acetamide<br><br>colorless solid | (2S)-2-(tert-butoxycarbonylamino)-2-phenyl-acetic acid (to be used in step [A])<br>2-(3,5-difluorophenoxy)acetic acid (to be used in step [C]) | (M + H2O)+<br>491.2 |

TABLE 2-continued

| Ex | Name Aspect | Reactant | MS (M + H+) |
|---|---|---|---|
| 66 | (2S)-2-[[(2S/R)-3-Cyclohexyl-2-(3,5-dichlorophenoxy)propanoyl]amino]-3-phenyl-N-[(3S)-1,1,1-trifluoro-4-methyl-2-oxopentan-3-yl]propanamide<br><br>colorless solid | 3-cyclohexyl-2-(3,5-dichlorophenoxy)propanoic acid (intermediate B-7 to be used in step [C]) | 615.3 |
| 67 | (2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyrazin-2-ylpropanamide<br><br>colorless solid | (2S)-2-(tert-butoxycarbonylamino)-2-phenyl-acetic acid (to be used in step [A])<br>2-(3,5-dichlorophenoxy)-3-(pyrazin-2-yl)propanoic acid (intermediate B-11 to be used in step [C])<br>Purified by HPLC chromatography | (M − H+)−<br>595.3 |
| 68 | (2R or 2S)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyrazin-2-ylpropanamide<br><br>colorless solid | (2S)-2-(tert-butoxycarbonylamino)-2-phenyl-acetic acid (to be used in step [A])<br>2-(3,5-dichlorophenoxy)-3-(pyrazin-2-yl)propanoic acid (intermediate B-11 to be used in step [C])<br>Purified by HPLC chromatography | (M − H+)−<br>595.4 |

TABLE 2-continued

| Ex | Name Aspect | Reactant | MS (M + H⁺) |
|---|---|---|---|
| 69 | (2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-2-ylpropanamide<br><br>colorless solid | (2S)-2-(tert-butoxycarbonylamino)-2-phenyl-acetic acid (to be used in step [A])<br>2-(3,5-dichlorophenoxy)-3-(2-pyridyl)propanoic acid (intermediate B-12 to be used in step [C])<br>Purified by HPLC chromatography | (M + H2O)+ 614.3 |
| 70 | (2R or 2S)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-3-ylpropanamide<br><br>colorless solid | (2S)-2-(tert-butoxycarbonylamino)-2-phenyl-acetic acid (to be used in step [A])<br>2-(3,5-dichlorophenoxy)-3-(2-pyridyl)propanoic acid (intermediate B-12 to be used in step [C])<br>Purified by HPLC chromatography | (M + H2O)+ 614.3 |
| 71 | (2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-3-ylpropanamide<br><br>colorless solid | (2S)-2-(tert-butoxycarbonylamino)-2-phenyl-acetic acid (to be used in step [A])<br>lithium 2-(3,5-dichlorophenoxy)-3-(pyridin-3-yl)propanoate (intermediate B-13 to be used in step [C])<br>Purified by HPLC chromatography | (M + H2O)+ 614.3 |

TABLE 2-continued

| Ex | Name Aspect | Reactant | MS (M + H+) |
|---|---|---|---|
| 72 | (2R or 2S)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-3-ylpropanamide<br>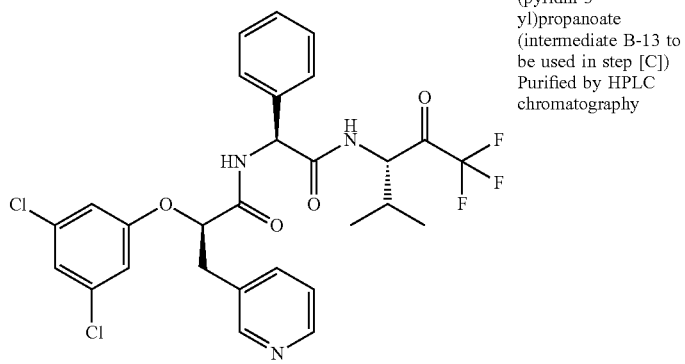<br>colorless solid | (2S)-2-(tert-butoxycarbonylamino)-2-phenyl-acetic acid (to be used in step [A]) lithium 2-(3,5-dichlorophenoxy)-3-(pyridin-3-yl)propanoate (intermediate B-13 to be used in step [C]) Purified by HPLC chromatography | (M + H2O)+ 614.3 |

The following examples listed in Table 3 were prepared in analogy to the procedures described for the preparation of example 1 and intermediate A-1 by using the (2S)-2-(tert-butoxycarbonylamino)-2-(4-methoxyphenyl)acetic acid in step [A] and the indicated starting material in step [C]:

TABLE 3

| Ex | Name Aspect | Reactant | MS (M + H+) |
|---|---|---|---|
| 73 | (2S or 2R)-(3,5-Dichlorophenoxy)-N-[(1S)-1-(4-methoxyphenyl)-2-oxo-2-[[(3S)-1,1,1-trifluoro-4-methyl-2-oxopentan-3-yl]amino]ethyl]-3-pyridin-2-ylpropanamide<br>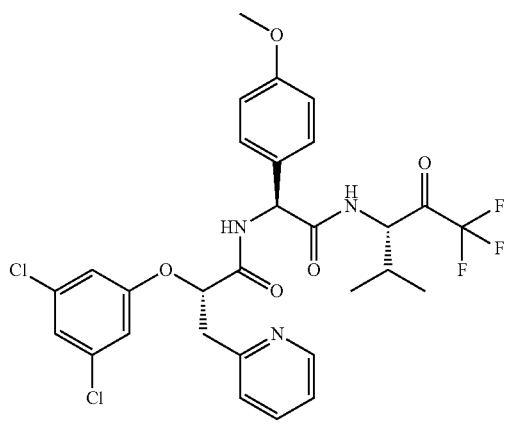<br>colorless waxy solid | 2-(3,5-dichlorophenoxy)-3-(2-pyridyl)propanoic acid (intermediate B-12 to be used in step [C]) Purified by HPLC chromatography | (M + H2O)+ 644.3 |

TABLE 3-continued

| Ex | Name Aspect | Reactant | MS (M + H⁺) |
|---|---|---|---|
| 74 | (2R or 2S)-(3,5-Dichlorophenoxy)-N-[(1S)-1-(4-methoxyphenyl)-2-oxo-2-[[(3S)-1,1,1-trifluoro-4-methyl-2-oxopentan-3-yl]amino]ethyl]-3-pyridin-2-ylpropanamide<br>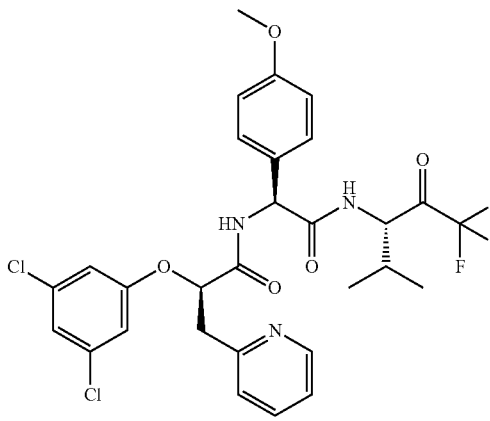<br>colorless waxy solid | 2-(3,5-dichlorophenoxy)-3-(2-pyridyl)propanoic acid (intermediate B-12 to be used in step [C]) Purified by HPLC chromatography | (M + H₂O)⁺ 644.3 |
| 75 | (2S or 2R)-(3,5-Dichlorophenoxy)-N-((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide<br>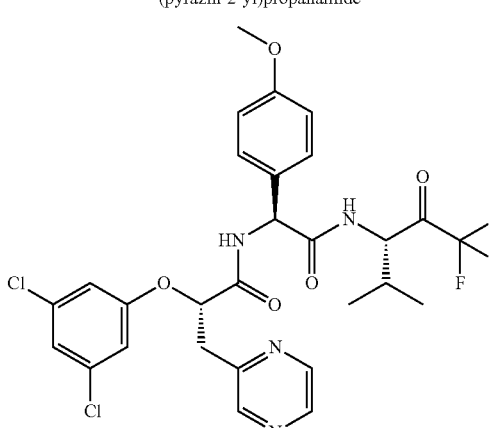<br>colorless waxy solid | 2-(3,5-dichlorophenoxy)-3-(pyrazin-2-yl)propanoic acid (intermediate B-11 to be used in step [C]) Purified by HPLC chromatography | (M + H₂O)⁺ 645.4 |

TABLE 3-continued

| Ex | Name<br>Aspect | Reactant | MS<br>(M + H⁺) |
|---|---|---|---|
| 76 | (2R or 2S)-(3,5-Dichlorophenoxy)-N-((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide<br>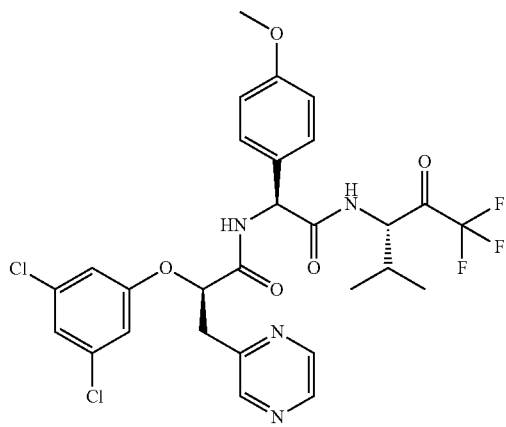<br>colorless waxy solid | 2-(3,5-dichlorophenoxy)-3-(pyrazin-2-yl)propanoic acid (intermediate B-11 to be used in step [C])<br>Purified by HPLC chromatography | (M + H₂O)⁺<br>645.4 |
| 77 | (S)-2-(2-(3-Cyanophenoxy)acetamido)-2-(4-methoxyphenyl)-N-((S)-1,1,1-trifluoro-4-methyl-2-oxopentan-3-yl)acetamide<br>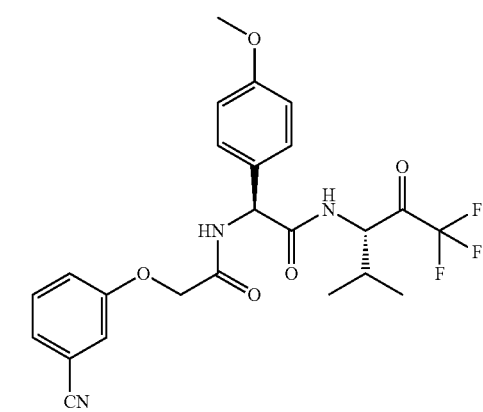<br>colorless solid | 2-(3-cyanophenoxy)acetic acid (to be used in step [C]) | 492.3 |

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

We claim:
1. A compound of formula (I)

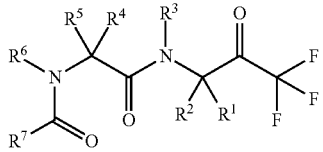

wherein
R¹ is alkyl, haloalkyl or cycloalkyl;
R² is hydrogen, alkyl, haloalkyl or cycloalkyl;
R³ is hydrogen, alkyl or cycloalkyl;
R⁴ is optionally substituted aryl, optionally substituted arylalkyl, optionally substituted heteroaryl or optionally substituted heteroarylalkyl, wherein each moiety is optionally substituted by one to three substituents independently selected from halogen, alkyl, haloalkyl, cycloalkyl, cyano, hydroxy, alkoxy or haloalkoxy;
R⁵ is H, alkyl, haloalkyl or cycloalkyl;
R⁶ is H, alkyl or cycloalkyl;
R⁷ is optionally substituted adamantanylalkyl, optionally substituted cycloalkyl, optionally substituted cycloalkylalkyl, optionally substituted dicycloalkylalkyl, optionally substituted heterocycloalkylarylalkyl, optionally substituted aryloxycycloalkylalkyl, optionally substituted aryl, optionally substituted arylalkyl, optionally substituted arylalkenyl, optionally substituted diarylalkyl, optionally substituted aryloxyalkyl, optionally substituted diaryloxyalkyl, optionally substituted arylaryloxyalkyl, optionally substituted heteroaryl, optionally substituted heteroarylalkyl, optionally substituted heteroarylalkenyl, optionally substituted arylheteroarylalkyl or optionally substituted aryloxyheteroarylalkyl, wherein the optional substituents are one to three groups independently selected from halogen, alkyl, haloalkyl, cycloalkyl, cyano, hydroxy, alkoxy, haloalkoxy or phenyl;
or a pharmaceutically acceptable salt thereof.

2. The compound according to claim 1, wherein
R¹ is alkyl, haloalkyl or cycloalkyl;
R² is hydrogen, alkyl, haloalkyl or cycloalkyl;
R³ is hydrogen, alkyl or cycloalkyl;
R⁴ is optionally substituted aryl, optionally substituted arylalkyl, optionally substituted heteroaryl or optionally substituted heteroarylalkyl, wherein the optional substituents are one to three groups independently selected from halogen, alkyl, haloalkyl, cycloalkyl, cyano, hydroxy, alkoxy or haloalkoxy;
R⁵ is hydrogen, alkyl, haloalkyl or cycloalkyl;
R⁶ is hydrogen, alkyl or cycloalkyl;
R⁷ is optionally substituted adamantanylalkyl, optionally substituted cycloalkyl, optionally substituted cycloalkylalkyl, optionally substituted dicycloalkylalkyl, optionally substituted aryl, optionally substituted arylalkyl, optionally substituted arylalkenyl, optionally substituted diarylalkyl, optionally substituted aryloxyalkyl, optionally optionally substituted diaryloxyalkyl, optionally substituted arylaryloxyalkyl, optionally substituted heteroaryl, optionally substituted heteroarylalkyl, optionally substituted heteroarylalkenyl, optionally substituted arylheteroarylalkyl or optionally substituted aryloxyheteroarylalkyl, wherein the optional substituents are one to three groups independently selected from halogen, alkyl, haloalkyl, cycloalkyl, cyano, hydroxy, alkoxy, haloalkoxy or phenyl;
or a pharmaceutically acceptable salt thereof.

3. The compound according to claim 1 wherein R¹ is alkyl.

4. The compound according to claim 1 wherein R² is hydrogen.

5. The compound according to claim 1 wherein R³ is hydrogen and alkyl.

6. The compound according to claim 1 wherein R³ is hydrogen.

7. The compound according to claim 1 wherein R⁴ is optionally substituted phenyl, optionally substituted phenylalkyl or optionally substituted pyridinylalkyl, wherein the optional substituents are one to three groups independently selected from alkoxy or halogen.

8. The compound according to claim 7 wherein R⁴ phenylalkyl optionally substituted by one halogen or phenyl optionally substituted by one alkoxy.

9. The compound according to claim 8 wherein R⁴ is phenylmethyl, phenyl, methoxyphenyl or chlorophenylmethyl.

10. The compound according to claim 1 wherein R¹ is alkyl, R² is hydrogen, R³ is hydrogen or alkyl, and R⁴ is phenylalkyl optionally substituted by one halogen or phenyl optionally substituted by one alkoxy.

11. The compound according to claim 1 wherein R⁵ is hydrogen.

12. The compound according to claim 1 wherein R⁶ is hydrogen.

13. The compound according to claim 1 wherein R¹ is alkyl, R², R⁵ and R⁶ are hydrogen, R³ is hydrogen or alkyl and R⁴ phenylalkyl optionally substituted by one halogen or phenyl optionally substituted by one alkoxy.

14. The compound according to claim 1 wherein R⁷ is optionally substituted adamantanylalkyl, optionally substituted cycloalkylalkyl, optionally substituted 1,1-dioxo-1,4-thiazinanylphenylalkyl, optionally substituted phenoxycycloalkylalkyl, optionally substituted phenylalkyl, optionally substituted phenylalkenyl, optionally substituted diphenylalkyl, optionally substituted phenoxyalkyl, optionally substituted phenylphenoxyalkyl, optionally substituted benzofuranyl or optionally substituted benzothiophenyl, wherein the optional substituents are one to three groups independently selected from halogen, alkoxy or phenyl.

15. The compound according to claim 1 wherein R⁷ is optionally substituted adamantanylalkyl, optionally substituted cycloalkylalkyl, optionally substituted phenylalkyl, optionally substituted phenylalkenyl, optionally substituted diphenylalkyl, optionally substituted phenoxyalkyl, optionally substituted phenylphenoxyalkyl, optionally substituted benzofuranyl or optionally substituted benzothiophenyl, wherein the optional substituents are one to three groups independently selected from halogen, alkoxy or phenyl.

16. The compound according to claim 1 wherein R⁷ is, dichlorophenoxymethyl, dichlorophenylethyl, 1,1-dioxo-1,4-thiazinanyl-dichlorophenylethyl or dichlorophenylethylenyl.

17. The compound according to claim 1 wherein R⁷ is dichlorophenoxymethyl or dichlorophenylethylenyl.

18. The compound according to claim 1 wherein the compound is of formula (Ia)

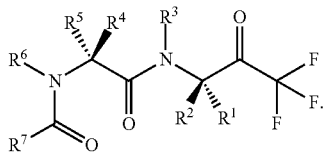

(Ia)

19. The compound according to claim 1 wherein
R$^1$ is alkyl;
R$^2$, R$^3$, R$^5$ and R$^6$ are hydrogen;
R$^4$ is phenylalkyl optionally substituted by one halogen or phenyl optionally substituted by one alkoxy;
R$^7$ is optionally substituted 1,1-dioxo-1,4-thiazinanylphenylalkyl, optionally substituted phenylalkyl, optionally substituted phenylalkenyl, optionally substituted diphenylalkyl, optionally substituted phenoxyalkyl or optionally substituted phenylphenoxyalkyl, wherein the optional substituents are one to three independently selected halogens;
or, a pharmaceutically acceptable salt thereof.

20. The compound according to claim 18 wherein
R$^1$ is alkyl;
R$^2$, R$^3$, R$^5$ and R$^6$ are hydrogen;
R$^4$ is phenylalkyl optionally substituted by a halogen or phenyl optionally substituted by one alkoxy;
R$^7$ is optionally substituted 1,1-dioxo-1,4-thiazinanylphenylalkyl, optionally substituted phenylalkyl, optionally substituted phenylalkenyl, optionally substituted diphenylalkyl, optionally substituted phenoxyalkyl or optionally substituted phenylphenoxyalkyl, wherein the optional substituents are one to three groups independently selected halogen substituents;
or, a pharmaceutically acceptable salt thereof.

21. The compound according to claim 1 wherein
R$^1$ is alkyl;
R$^2$, R$^3$, R$^5$ and R$^6$ are hydrogen;
R$^4$ is phenylalkyl optionally substituted by one halogen or phenyl optionally substituted one alkoxy;
R$^7$ is optionally substituted phenylalkenyl, optionally substituted diphenylalkyl, optionally substituted phenoxyalkyl or optionally substituted phenylphenoxyalkyl, wherein the optional substituents are one to three independently selected halogen substituents;
or, a pharmaceutically acceptable salt thereof.

22. The compound according to claim 18 wherein
R$^1$ is alkyl;
R$^2$, R$^3$, R$^5$ and R$^6$ are hydrogen;
R$^4$ is phenylalkyl optionally substituted by on halogen or phenyl optionally substituted by one alkoxy;
R$^7$ is optionally substituted phenylalkenyl, optionally substituted diphenylalkyl, optionally substituted phenoxyalkyl or optionally substituted phenylphenoxyalkyl, wherein the optional substituents are one to three groups independently selected halogen substituents;
or, a pharmaceutically acceptable salt thereof.

23. The compound according to claim 1 which compound is selected from the group consisting of:
(2R)-2-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-phenylpropanamide;
(2R/S)-(3,4-Dichlorophenyl)-3-(3,4-dichlorophenyl)-N-[(1S and 1R)-2-oxo-1-phenyl-2-[[(3S)-1,1,1-trifluoro-4-methyl-2-oxopentan-3-yl]amino]ethyl]propanamide;
(3R or 3S)-(4-Chlorophenyl)-2-(4-methoxyphenyl)-N-[(1S and 1R)-2-oxo-1-phenyl-2-[[(3S)-1,1,1-trifluoro-4-methyl-2-oxopentan-3-yl]amino]ethyl]propanamide;
(3S or 3R)-(4-Chlorophenyl)-2-(4-methoxyphenyl)-N-[(1S and 1R)-2-oxo-1-phenyl-2-[[(3S)-1,1,1-trifluoro-4-methyl-2-oxopentan-3-yl]amino]ethyl]propanamide;
(3S or 3R)-(3,4-Dichlorophenyl)-3-(1,1-dioxo-1,4-thiazinan-4-yl)-N-[(1S and 1R)-2-oxo-1-phenyl-2-[[(3S)-1,1,1-trifluoro-4-methyl-2-oxopentan-3-yl]amino]ethyl]propanamide;
(3R or 3S)-(3,4-Dichlorophenyl)-3-(1,1-dioxo-1,4-thiazinan-4-yl)-N-[(1S and 1R)-2-oxo-1-phenyl-2-[[(3S)-1,1,1-trifluoro-4-methyl-2-oxopentan-3-yl]amino]ethyl]propanamide;
(S)-2-(3-(3,5-Difluorophenyl)propanamido)-3-phenyl-N—((S)-1,1,1-trifluoro-4-methyl-2-oxopentan-3-yl)propanamide;
(R)-2-(3,5-Dichlorophenoxy)-N—((S)-1-oxo-3-phenyl-1-(((S)-1,1,1-trifluoro-4-methyl-2-oxopentan-3-yl)amino)propan-2-yl)-3-phenylpropanamide;
3-(3,5-Difluorophenyl)-N-[(1S and 1R)-2-oxo-1-phenyl-2-[[(3S)-1,1,1-trifluoro-4-methyl-2-oxopentan-3-yl]amino]ethyl]propanamide;
(R)-2-(3,5-Difluorophenoxy)-N-((1S and 1R)-2-oxo-1-phenyl-2-(((S)-1,1,1-trifluoro-4-methyl-2-oxopentan-3-yl)amino)ethyl)-3-phenylpropanamide;
(3R/S)-Cyclohexyl-2-(3,5-dichlorophenoxy)-N-[(1S and 1R)-2-oxo-1-phenyl-2-[[(3S)-1,1,1-trifluoro-4-methyl-2-oxopentan-3-yl]amino]ethyl]propanamide;
(2S and 2R)-2-[[2-(3,5-Difluorophenoxy)acetyl]amino]-2-phenyl-N-[(3S)-1,1,1-trifluoro-4-methyl-2-oxopentan-3-yl]acetamide;
(2S)-2-[[(2S/R)-3-Cyclohexyl-2-(3,5-dichlorophenoxy)propanoyl]amino]-3-phenyl-N-[(3S)-1,1,1-trifluoro-4-methyl-2-oxopentan-3-yl]propanamide;
(2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyrazin-2-ylpropanamide;
(2R or 2S)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyrazin-2-ylpropanamide;
(2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-2-ylpropanamide;
(2R or 2S)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-3-ylpropanamide;
(2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-3-ylpropanamide;
(2R or 2S)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-3-ylpropanamide;
(2S or 2R)-(3,5-Dichlorophenoxy)-N-[(1S)-1-(4-methoxyphenyl)-2-oxo-2-[[(3S)-1,1,1-trifluoro-4-methyl-2-oxopentan-3-yl]amino]ethyl]-3-pyridin-2-ylpropanamide;
(2R or 2S)-(3,5-Dichlorophenoxy)-N-[(1S)-1-(4-methoxyphenyl)-2-oxo-2-[[(3S)-1,1,1-trifluoro-4-methyl-2-oxopentan-3-yl]amino]ethyl]-3-pyridin-2-ylpropanamide;
(2S or 2R)-(3,5-Dichlorophenoxy)-N—((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide;

(2R or 2S)-(3,5-Dichlorophenoxy)-N—((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide; and, (S)-2-(2-(3-Cyanophenoxy)acetamido)-2-(4-methoxyphenyl)-N—((S)-1,1,1-trifluoro-4-methyl-2-oxopentan-3-yl)acetamide;

or, a pharmaceutically acceptable salt thereof.

24. The compound according to claim 1 which compound is selected from the group consisting of:

(2R)-2-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-phenylpropanamide;

(2S or 2R)-(3,5-Dichlorophenoxy)-N-[(1S and 1R)-2-oxo-1-phenyl-2-[[(3S)-1,1,1-trifluoro-4-methyl-2-oxopentan-3-yl]amino]ethyl]-3-pyridin-2-ylpropanamide;

(2R or 2S)-(3,5-Dichlorophenoxy)-N-[(1S)-1-(4-methoxyphenyl)-2-oxo-2-[[(3S)-1,1,1-trifluoro-4-methyl-2-oxopentan-3-yl]amino]ethyl]-3-pyridin-2-yl-propanamide; and, (2S or 2R)-(3,5-Dichlorophenoxy)-N—((S)-1-(4-methoxyphenyl)-2-oxo-2-(((S)-1,1,1-trifluoro-4-methyl-2-oxopentan-3-yl)amino)ethyl)-3-(pyrazin-2-yl)propanamide;

or, a pharmaceutically acceptable salt thereof.

25. A process to prepare a compound according to claim 1 comprising oxidizing a compound of formula (II)

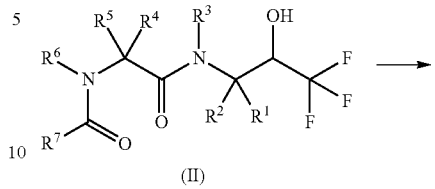

(II)

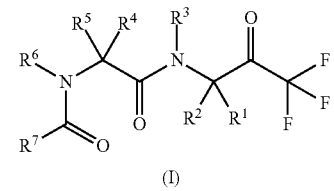

(I)

wherein IV, $R^2$, $R^3$, $R^4$, $R^5$, $R^6$ and $R^7$ are as defined in any of claim 1.

26. A pharmaceutical composition comprising a compound according to claim 1 and at least one pharmaceutically acceptable carrier, diluent or excipient.

* * * * *